US012324691B2

(12) United States Patent
McCarthy et al.

(10) Patent No.: US 12,324,691 B2
(45) Date of Patent: Jun. 10, 2025

(54) CONE BEAM COMPUTED TOMOGRAPHY CENTERING WITH AUGMENTED REALITY

(71) Applicant: GE Precision Healthcare LLC, Wauwatosa, WI (US)

(72) Inventors: Thomas McCarthy, Charente (FR); François Kotian, Yvelines (FR); Yves Trousset, Yvelines (FR)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 239 days.

(21) Appl. No.: 18/057,177

(22) Filed: Nov. 18, 2022

(65) Prior Publication Data

US 2024/0164730 A1 May 23, 2024

(51) Int. Cl.

| | |
|---|---|
| ***A61B 6/03*** | (2006.01) |
| ***A61B 6/00*** | (2006.01) |
| ***A61B 6/40*** | (2024.01) |
| ***A61B 6/46*** | (2024.01) |
| *A61B 90/00* | (2016.01) |
| *A61N 5/10* | (2006.01) |

(52) U.S. Cl.

CPC ................ *A61B 6/03* (2013.01); *A61B 6/032* (2013.01); *A61B 6/035* (2013.01); *A61B 6/037* (2013.01); *A61B 6/4085* (2013.01); *A61B 6/4435* (2013.01); *A61B 6/4441* (2013.01); *A61B 6/462* (2013.01); *A61B 6/466* (2013.01); *A61B 6/469* (2013.01); *A61B 2090/365* (2016.02); *A61N 5/1049* (2013.01)

(58) Field of Classification Search

CPC ........... A61B 6/03; A61B 6/032; A61B 6/035; A61B 6/037; A61B 6/10; A61B 6/102; A61B 6/12; A61B 6/44; A61B 6/4405; A61B 6/4429; A61B 6/4435; A61B 6/4441; A61B 6/4447; A61B 6/4476; A61B 6/4482; A61B 6/46; A61B 6/461; A61B 6/462; A61B 6/463; A61B 6/464; A61B 6/465; A61B 6/466; A61B 6/467; A61B 6/469; A61B 2090/364; A61B 2090/365

USPC ........ 378/4, 15, 20, 189, 196–198, 205, 209

See application file for complete search history.

(56) References Cited

U.S. PATENT DOCUMENTS

| | | | |
|---|---|---|---|
| 5,442,674 | A | 8/1995 | Picard et al. |
| 7,559,694 | B2 | 7/2009 | Gorges et al. |
| 8,180,132 | B2 | 5/2012 | Gorges et al. |
| 8,182,150 | B2 | 5/2012 | Gorges et al. |
| 10,154,823 | B2 | 12/2018 | Von Berg et al. |

(Continued)

FOREIGN PATENT DOCUMENTS

| | | | |
|---|---|---|---|
| CN | 110199357 | A | 9/2019 |
| RU | 2017106184 | A | 8/2018 |

*Primary Examiner* — Allen C. Ho
(74) *Attorney, Agent, or Firm* — McCoy Russell LLP

(57) ABSTRACT

Methods for an imaging system are provided. In some examples, a method includes determining an imaging field of view (FOV) of a rotatable imaging system, determining a size and/or shape of the imaging FOV and a position of the imaging FOV relative to the rotatable imaging system, determining a first location of the imaging FOV relative to an environment in which the rotatable imaging system is positioned, and sending information indicating the size and/or shape and the position of the imaging FOV as well as the first location of the imaging FOV relative to the environment to an external computing device.

20 Claims, 15 Drawing Sheets

(56) References Cited

U.S. PATENT DOCUMENTS

| | | | | |
|---|---|---|---|---|
| 10,299,740 | B2 * | 5/2019 | McCarthy | A61B 6/102 |
| 10,366,489 | B2 * | 7/2019 | Boettger | G06T 7/50 |
| 10,573,023 | B2 | 2/2020 | Crawford et al. | |
| 10,667,869 | B2 * | 6/2020 | Kotian | A61B 6/032 |
| 10,709,398 | B2 * | 7/2020 | Schweizer | A61B 34/25 |
| 10,925,562 | B2 * | 2/2021 | McCarthy | A61B 6/4452 |
| 11,045,151 | B2 * | 6/2021 | Jensen | A61B 6/4085 |
| 11,100,668 | B2 * | 8/2021 | Crawford | G06F 3/011 |
| 11,123,025 | B2 | 9/2021 | Ruijters et al. | |
| 11,229,409 | B2 * | 1/2022 | Deutschmann | A61B 6/462 |
| 11,311,267 | B2 * | 4/2022 | Schweizer | A61B 6/469 |
| 11,596,373 | B2 * | 3/2023 | Glatz | A61B 6/4064 |
| 11,654,304 | B2 * | 5/2023 | Chen | A61B 6/0492<br>382/103 |
| 11,701,183 | B2 * | 7/2023 | Martin, III | A61B 34/20 |
| 11,766,232 | B2 * | 9/2023 | Hannemann | A61B 5/70<br>378/207 |
| 11,786,206 | B2 * | 10/2023 | Steines | A61B 90/37<br>378/91 |
| 11,813,094 | B2 * | 11/2023 | Helm | A61B 6/032 |
| 12,023,187 | B2 * | 7/2024 | Helm | A61B 6/032 |
| 12,076,172 | B2 * | 9/2024 | Helm | A61B 6/4085 |
| 2018/0116613 | A1 | 5/2018 | Von Berg et al. | |

* cited by examiner

CONE BEAM COMPUTED TOMOGRAPHY CENTERING WITH AUGMENTED REALITY

FIELD

The present disclosure is related to the field of non-invasive imaging. More specifically the present disclosure is directed to systems and methods of cone beam computed tomography centering with augmented reality.

BACKGROUND

In medical x-ray imaging, for example, angiographic systems, an x-ray signal transmitter and an x-ray detector may be mounted on opposing ends of a substantially C-shaped gantry such that x-rays emitted by the signal transmitter in a beam are incident on and detectable by the x-ray detector. The signal transmitter and the detector are positioned such that when an object (e.g., part of a human body) is interposed there between and is irradiated with x-rays, the detector produces data representative of characteristics of the interposed object. The data produced is typically displayed on a monitor or electronically stored.

The C-arm gantry defines an axis of rotation about which the signal transmitter and detector are rotatable. By positioning this axis of rotation at or near an object, and by rotating the signal transmitter and detector about the object, or rotating the object about the signal transmitter and detector, images of the object taken at a plurality of different orientations can be obtained. These images can be combined to generate a comprehensive three-dimensional image of the object, for example using methods of image reconstruction. Such acquisitions are usually called cone-beam computed tomography (CBCT) acquisitions.

BRIEF DESCRIPTION

In one aspect, the present disclosure relates to various methods for an imaging system including determining an imaging field of view (FOV) of a rotatable imaging system including determining a size and/or shape of the imaging FOV and a position of the imaging FOV relative to the rotatable imaging system. The method may also include determining a first location of the imaging FOV relative to an environment in which the rotatable imaging system is positioned and sending information indicating the size and/or shape and the position of the imaging FOV as well as the first location of the imaging FOV relative to the environment to an external computing device.

For example, the external computing device may be an augmented reality device that may display graphical representations of the imaging FOV. Further, in some examples, the rotatable imaging system may determine a position of a target anatomy of the patient and send the positon of the target anatomy to the augmented reality device for display on the augmented reality device, in order to aid in positioning the patient to position the target anatomy within the imaging FOV.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
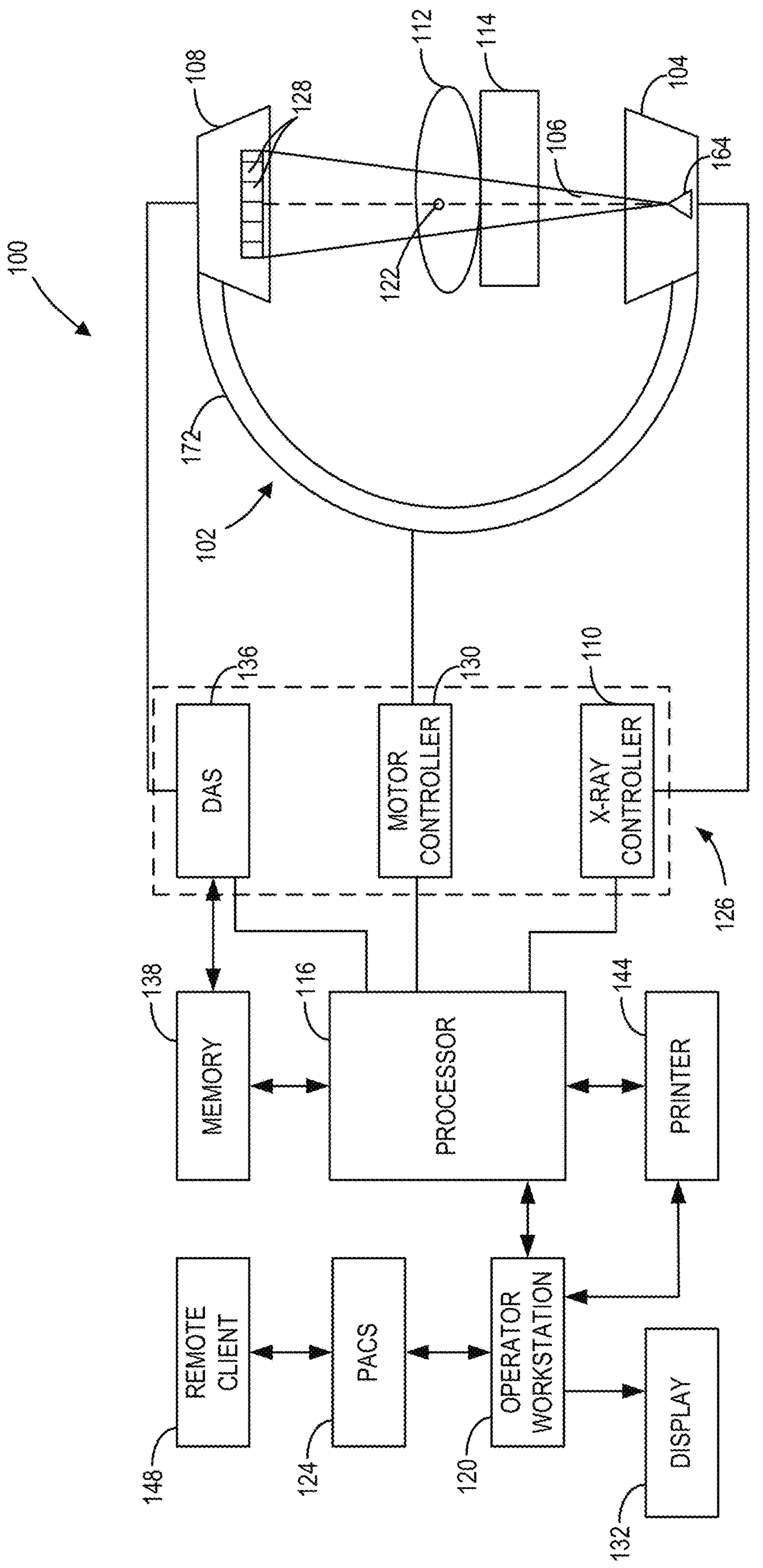
FIG. 1 shows an example C-arm cone beam computed tomography (CBCT) imaging system.

Embodiments of the present disclosure will now be described, by way of example, with reference to the FIGS. 1-16, which relate to various embodiments for computing a rotational trajectory of an imaging system, computing an imaging field of view (FOV) from the rotational trajectory, computing a first location of the imaging FOV, and sending the data indicating the size, shape, and first location of the imaging FOV to an external computing device. The external computing device may be an augmented reality (AR) device that may display an overlay of the imaging FOV in the first position. When working with medical imaging scanner systems, it may not be safe for users to assume that the pathway of components that move during medical imaging is clear, since the components may collide with a patient or other equipment. One approach for avoiding such collisions is for a user to visually estimate whether components of the scanner system will be clear of collisions along their range of motion and, if not, to then stop a scan, adjust positioning of the scanner system and/or object in the pathway, and re-start imaging. Another, more often used, approach is for a user to perform a dry run in which the scanner system moves through its entire pathway while the user observes for possible collisions, and while the signal transmitter is unpowered. These approaches undesirably consume time, personnel resources, and electrical power.

Cone beam computed tomography (CBCT) capable systems typically provide a small imaging FOV and thus can three dimensionally image only a relatively small portion of an object (e.g. patient) during a single scan. When imaging an off-center portion of an object, for example, a liver of a patient, the table upon which the patient rests during the scan is typically positioned such that the anatomy of interest coincides with the three dimensional (3-D) FOV. However, it is possible that the detector and/or the signal transmitter may collide with the patient during scanning (e.g., during rotation of the detector and signal transmitter) because the patient is now positioned closer to the trajectories of the detector and/or the signal transmitter. Moving the detector away from the center of the rotation reduces collision risk, but further reduces the diameter of any reconstructed 3-D image of the object.

Currently, imaging system operators use a trial-and-error approach wherein the patient is repositioned so that no such collisions occur. In some instances, repositioning the patient may lead to the region of interest (e.g., the target anatomy) lying outside of the imaging FOV. If the patient is imaged in these instances, then the patient needlessly receives a radiation dose because the region of interest is not actually imaged. Typically, finding the optimal position of the patient where no collisions occur and the region of interest is successfully imaged can take up to fifteen minutes of time. Reduced FOV or improper patient positioning can potentially lead to additional acquisition, resulting in increased x-ray dose, prolonged medical procedure duration, and/or additional use of a chemical injectable agent.

Various embodiments of the present disclosure are directed to an improved user interface for operating an imaging system having movable scanner components. The inventors herein provide a solution to the problem laid out above with a method of computing the rotational trajectory of the CBCT system in order to provide the optimal imaging FOV with the most intersection over the target anatomy, under image quality constraints for a patient position and/or radiation dosage constraints. An augmented reality (AR) system enables a user who is wearing an AR device or looking at a video monitor of the operating room scene to visually observe graphical objects that are displayed as an overlay on the imaging system to illustrate a virtual 3-D FOV representative of the 3-D FOV that may be imaged. The graphical objects may provide predictive visualization to the user of what the optimal 3-D FOV may be in relation to the subject being imaged. The image processing system may employ image processing algorithms to segment and localize the imaging system and extrapolate the trajectory of the imaging system according to the method.

Turning now to the figures, FIG. 1 illustrates an example imaging system 100 for acquiring and processing image data. In the illustrated embodiment, the imaging system 100 is a digital x-ray system designed both to acquire original image data and to process the image data for display. The imaging system 100 may be a stationary or mobile x-ray system. In the embodiment illustrated in FIG. 1, the imaging system 100 is depicted as a C-arm rotatable imaging system, yet it may be understood that other forms of imaging and/or navigation systems may be used within the scope of the present disclosure. For example, it may be understood that the present techniques may also be useful when applied to images acquired using other imaging modalities, such as fluoroscopic x-ray imaging, tomosynthesis, and so forth. The present discussion of a computed tomography imaging modality is provided merely as an example of one suitable imaging modality. For example, the imaging system 100 may be any imaging system that acquires two-dimensional images (e.g., slices or projections) of three-dimensional objects.

The imaging system 100 may be a rotatable imaging system and thus may acquire x-ray attenuation data at a variety of views around a patient and suitable for tomographic reconstruction. The imaging system 100 includes a signal transmitter 104 secured to a C-arm 172. The signal transmitter 104 may be an x-ray tube, a distributed x-ray source (such as a solid-state or thermionic x-ray source), or any other source of x-ray radiation suitable for the acquisition of medical or other images. The signal transmitter 104 may also be referred to as a radiation source. For example, the signal transmitter 104 may comprise an x-ray generator and x-ray tube. The signal transmitter 104 is configured to emit a beam of radiation 106 from a focal point 164 (e.g., a source) in the direction of a subject 112 (or object). For example, the subject 112 may be a patient. In the depicted embodiment, the beam of radiation 106 is emitted in a cone shape, e.g., a cone-beam. This cone-beam of x-rays pass through an imaged volume of the subject 112. An incident portion (also referred to as incident x-rays) of the beam of radiation 106 passes through or around the subject 112 and impacts (or impinges on) a detector 108. The detector 108 may also be referred to as a radiation detector. In the present example, the detector 108 is a digital x-ray detector and may be portable or permanently mounted to the imaging system 100. In certain embodiments, the detector 108 may convert the incident x-ray photons to lower energy photons which are detected. Electrical signals are generated in response to the detected photons, and these signals are processed to reconstruct images of the features (e.g., anatomical features) within the subject 112. Together, the signal transmitter 104 and the detector 108 comprise an x-ray imaging chain.

As an example, the detector 108 may include one or more complementary metal oxide semiconductor (CMOS) light imager panels, each separately defining an array of detector elements (e.g., pixels). Each detector element produces an electrical signal that represents the intensity of the x-ray beam incident at the position of the detector element when the beam strikes the detector 108. This signal may be digitized and sent to a monitor/display device for display. Accordingly, in one embodiment, the detector 108 may be fabricated in a multi-slice configuration including the plurality of rows of cells or detector elements 128. In such a configuration, one or more additional rows of the detector elements 128 are arranged in a parallel configuration for acquiring the projection data.

The signal transmitter 104 and the detector 108 may be controlled by a system controller 126 that provides both power and control signals for the operation of the imaging system 100. The system controller 126 may control the signal transmitter 104 via an x-ray controller 110, which may be a component of the system controller 126. In such an embodiment, the x-ray controller 110 may be configured to provide power and timing signals to the signal transmitter 104.

The detector 108 may further be connected to the system controller 126. The system controller 126 controls the acquisition of the signals generated by the detector 108. In some examples, the system controller 126 acquires the signals generated by the detector 108 using a data acquisition system (DAS) 136. The DAS 136 in some examples may be integrated within the detector 108.

Further, the detector 108 includes or communicates with control circuitry in the system controller 126 that commands acquisition of the signals generated in the detector 108. The detector 108 may communicate with the system controller 126 via any suitable wireless communication or through a cable or other mechanical connection. Alternatively, operational commands may be implemented within the detector 108 itself.

The system controller 126 is further operationally connected to the C-arm 172 as well as optionally to a table 114 configured to support the subject 112. A motor controller 130 of the system controller 126 provides instructions and commands to mechanical components of the C-arm 172 and in some examples also to the table 114 to carry out linear and/or rotational movement thereof. In other embodiments, the table 114 may have a separate controller (e.g., table motor controller 218) and/or the table may be moved manually. The linear and/or rotational movement of the C-arm 172 enables the signal transmitter 104 and the detector 108 to be rotated one or multiple turns about the subject 112, such as rotated primarily in an X-Y plane or angled with respect to the subject. The distance between the detector 108 and signal transmitter 104 may also be adjusted. Further, the table 114 supporting the subject 112 may be moved with respect to the movement of the C-arm 172 and/or predicted movement of the C-arm 172 to position the patient within the imaging FOV of the imaging system 100. Thus, movement of the patient and/or components of the imaging system to adjust the imaging FOV may include one or both of movement of the C-arm 172 and movement of the table 114.

In general, system controller 126 commands operation of the imaging system 100 (such as via the operation of the signal transmitter 104, the detector 108, and positioning systems described above) to execute examination protocols and to process acquired data. For example, the system controller 126, via the systems and controllers noted above, may rotate a rotatable gantry 102 supporting the signal transmitter 104 and the detector 108 about an area of interest or target T so that x-ray attenuation data may be obtained at a variety of views relative to a target anatomy (not pictured in FIG. 1). For example, an isocenter 122 of the beam of radiation 106 may be focused at the target anatomy. In the present example, the system controller 126 may also include signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 126 are provided to a processor 116 for reconstruction of images. The processor 116 may be one or more conventional microprocessors. The data collected by the DAS 136 may be transmitted to the processor 116 directly or after storage in a memory 138. Any type of memory suitable for storing data might be utilized by the imaging system 100. For example, the memory 138 may include one or more optical, magnetic, and/or solid state memory storage structures. Moreover, the memory 138 may be located at the acquisition system site and/or may include remote storage devices for storing data, processing parameters, and/or routines for image reconstruction, as described below. One example of image reconstruction may include cone beam computed tomography (CBCT) wherein images acquired at multiple angles about the subject 112 are projected against each other to form voxels of a 3-D representation of the imaged region. Other forms of image reconstruction, including but not limited to processing image data from the detector signal to produce clinically useful images, may be used.

The processor 116 may be configured to receive commands and scanning parameters from an operator via an operator workstation 120, typically equipped with a keyboard, touchscreen and/or other input devices. The operator may control the imaging system 100 via the operator workstation 120. Thus, the operator may observe the reconstructed images and/or otherwise operate the imaging system 100 using the operator workstation 120. For example, a display 132 coupled to the operator workstation 120 may be utilized to observe the reconstructed images and to control imaging (e.g., initiate image acquisition, set imaging parameters such as x-ray source current/voltage). Additionally, the images also may be printed by a printer 144 which may be coupled to the operator workstation 120.

Further, the processor 116 and operator workstation 120 may be coupled to other output devices, which may include standard or special purpose computer monitors and associated processing circuitry. One or more operator workstations 120 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Further, the operator workstation 120 may also be coupled to a picture archiving and communications system (PACS) 124. The PACS 124 may in turn be coupled to a remote client 148, radiology department information system (RIS), hospital information system (HIS) or to an internal or external network, so that others at different locations may gain access to the raw or processed image data.

While the preceding discussion has described the various components of the imaging system 100 separately, these various components may be provided within a common platform or in interconnected platforms. For example, the processor 116, the memory 138, and the operator workstation 120 may be provided collectively as a general or special purpose computer or workstation configured to operate in accordance with the aspects of the present disclosure. In such embodiments, the general or special purpose computer may be provided as a separate component with respect to the data acquisition components of the imaging system 100 or may be provided in a common platform with such components. Likewise, the system controller 126 may be provided as part of such a computer or workstation or as part of a separate system dedicated to image acquisition.

The imaging system 100 as shown in FIG. 1 may also include a variety of alternative embodiments without department from the scope of this disclosure. The table 114 may be fixed to the floor of the room via a pedestal but have movable and rotatable components. Alternatively, the imaging system 100 may be a mobile x-ray system with a portable table. In practice, the imaging system 100 may be any suitable x-ray based imaging system that is configured with cone beam x-rays and components rotatable about an isocenter (e.g., isocenter 122).

As used herein, the phrase "reconstructing an image" is not intended to exclude embodiments of the present invention in which data representing an image are generated but a viewable image is not. Therefore, as used herein, the term "image" broadly refers to both viewable images and data representing a viewable image. However, many embodiments generate (or are configured to generate) at least one viewable image.

As will be described in more detail below, the subject 112 may be imaged with the x-ray imaging chain, including the signal transmitter 104 and the detector 108. Although not explicitly shown, it may be understood that the x-ray imaging chain may further include various components (e.g., a collimator) and apertures. The x-ray imaging chain is positioned around the subject 112 at different angles that are chosen by an operator (e.g., a clinician). The subject 112 lays on the table 114, and the position of the table 114 may also change throughout the imaging. The acquired x-ray images are 2-D conic projections, and the changes to the imaging chain and the position of the table 114 may enable the operator to see an anatomy of the subject 112 under different angles and magnification factors. For example, a workflow of the imaging procedure may include acquiring several image sequences, which may be used to diagnose and if indicated, intervene on the subject 112. An anatomical place of interest may be viewed in these different images in real-time, which may help guide needle insertions or other interventions.

In some CT systems, the signal transmitter 104 (e.g., an x-ray source) and the detector 108 are rotated with the rotatable gantry 102 within the imaging plane and around the object to be imaged such that an angle at which the radiation beam intersects the object constantly changes. A group of x-ray radiation attenuation measurements, e.g., projection data, from the detector at one gantry angle is referred to as a "view." A "scan" of the object includes a set of views made at different gantry angles, or view angles, during one revolution of the signal transmitter and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

FIG. 1 illustrates the imaging system 100. In certain embodiments, the imaging system 100 is configured to traverse different angular positions around the subject 112 for acquiring desired projection data. Accordingly, the rotatable gantry 102 and the components mounted thereon may be configured to rotate about the isocenter 122 for acquiring the projection data. Alternatively, in embodiments where a projection angle relative to the subject 112 varies as a function of time, the mounted components may be configured to move along a general curve rather than along a segment of a circle.

As the signal transmitter 104 and the detector 108 rotate, the detector 108 collects data of the attenuated x-ray beams. The data collected by the detector 108 undergoes preprocessing and calibration to condition the data to represent the line integrals of the attenuation coefficients of the scanned subject 112. The processed data are commonly called projections.

In some examples, the individual detectors or detector elements 128 of the detector 108 may include photon-counting detectors which register the interactions of individual photons into one or more energy bins. It should be appreciated that the methods described herein may also be implemented with energy-integrating detectors.

In some examples, the display 132 allows the operator to evaluate the imaged anatomy. The display 132 may also allow the operator to select a volume of interest (VOI) and/or request patient information, for example, via a graphical user interface (GUI) for a subsequent scan or processing. The display 132 may also allow the operator to select points of interest on a particular scan for use in computer computations. For example, the user may select a point of anatomy on multiple 2-D x-ray images from different angles for which the computer can generate a coordinate system and a 3-D coordinate point, as will be described below.

Figure 2:
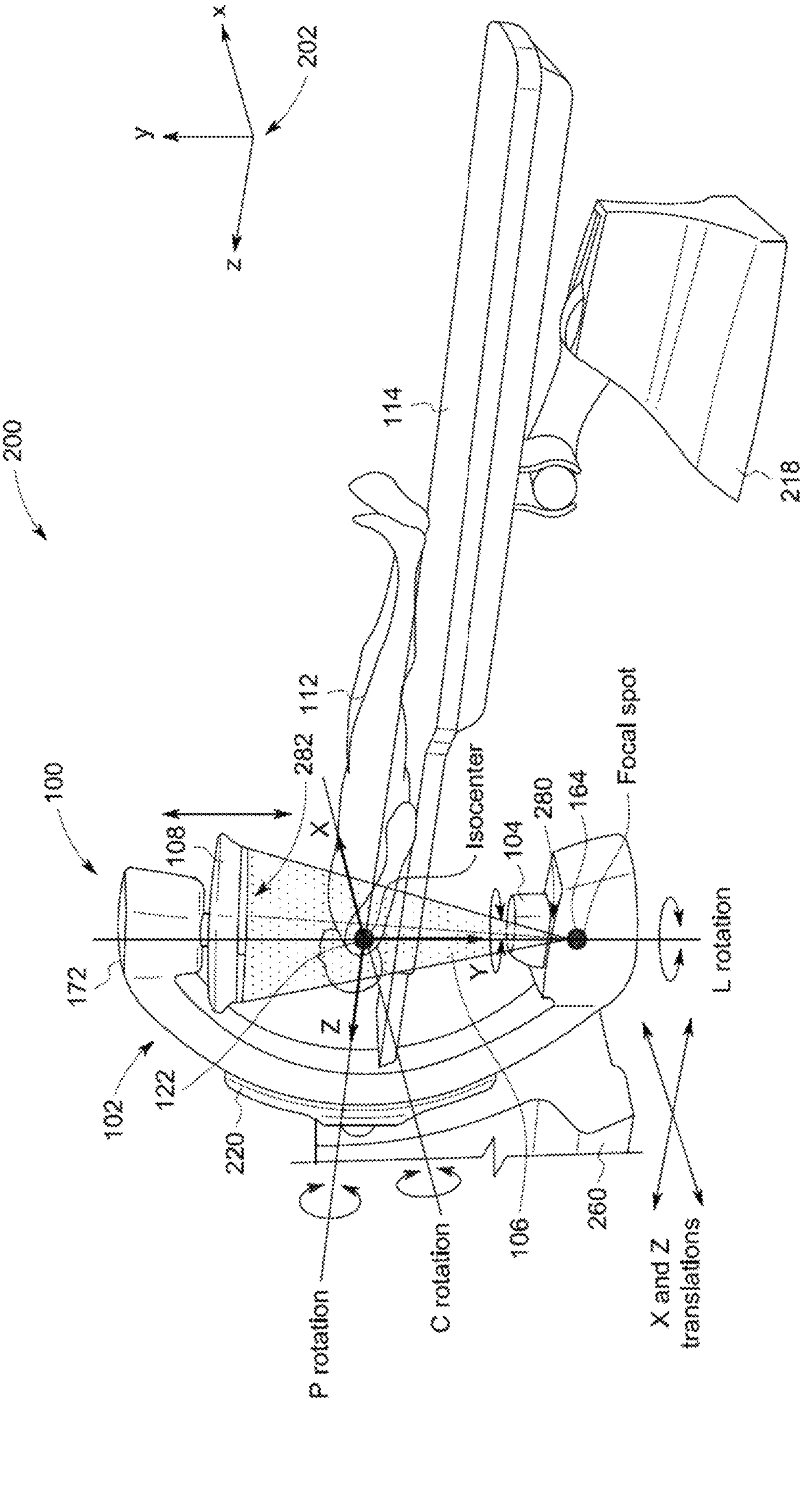
FIG. 2 is a perspective view of the imaging system of FIG. 1.

FIG. 2 is a schematic diagram drawing showing a perspective view 200 of aspects of the imaging system 100. The imaging system 100 may include a movable station 260 and the rotatable gantry 102. The rotatable gantry 102 may include the C-arm 172. The movable station 260 may include a vertical shaft (not pictured) and a gantry mount 220 which may be rotatably attached to the vertical shaft (not pictured). The movable station 260 may include a number of wheels that in some embodiments may be omni-directional (not pictured), which together may provide movement of the movable station 260 in any direction in an X-Y plane about the floor. The movable station 260 may include motors to provide one degree of freedom in rotation and two degrees of translation (the X-Y plane of the floor). There may be a pair of handles (not pictured) mounted to the movable station 260 that may allow a user to manually maneuver the movable station 260 about the floor. A motor (not pictured) may be attached to the vertical shaft. The motor may be designed to rotate the gantry mount 220 a full 360 degrees about a P axis, as shown in FIG. 1.

Figure 5:
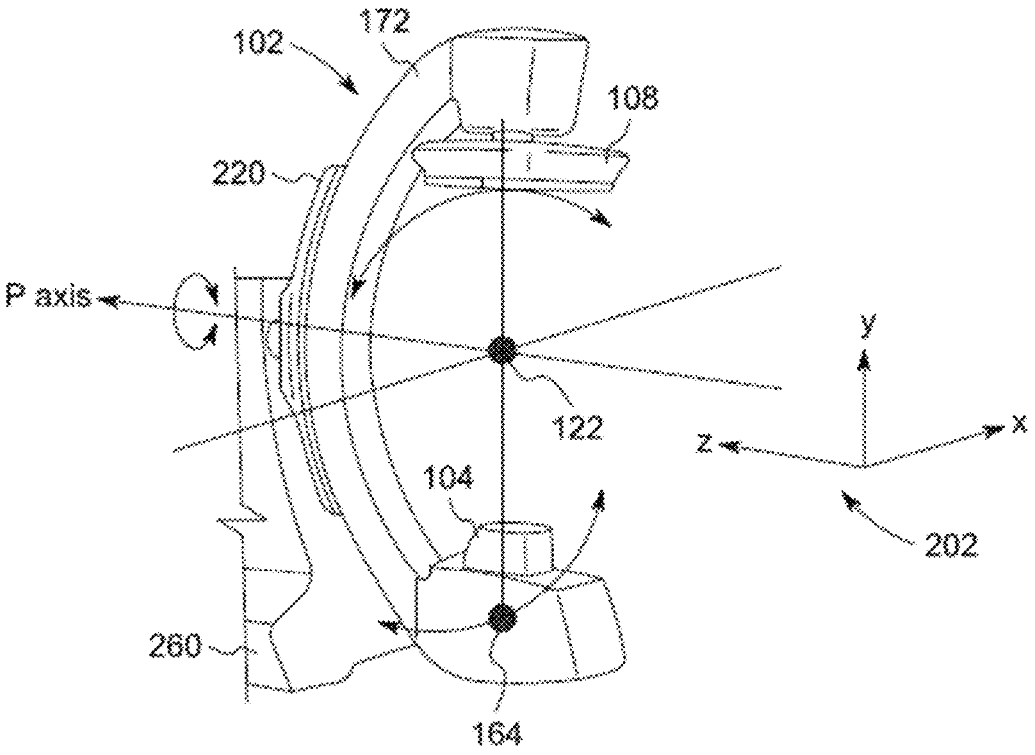
FIG. 5 schematically illustrates one of the two axes about which the C-arm can rotate, specifically depicting the P axis.
Figure 6:
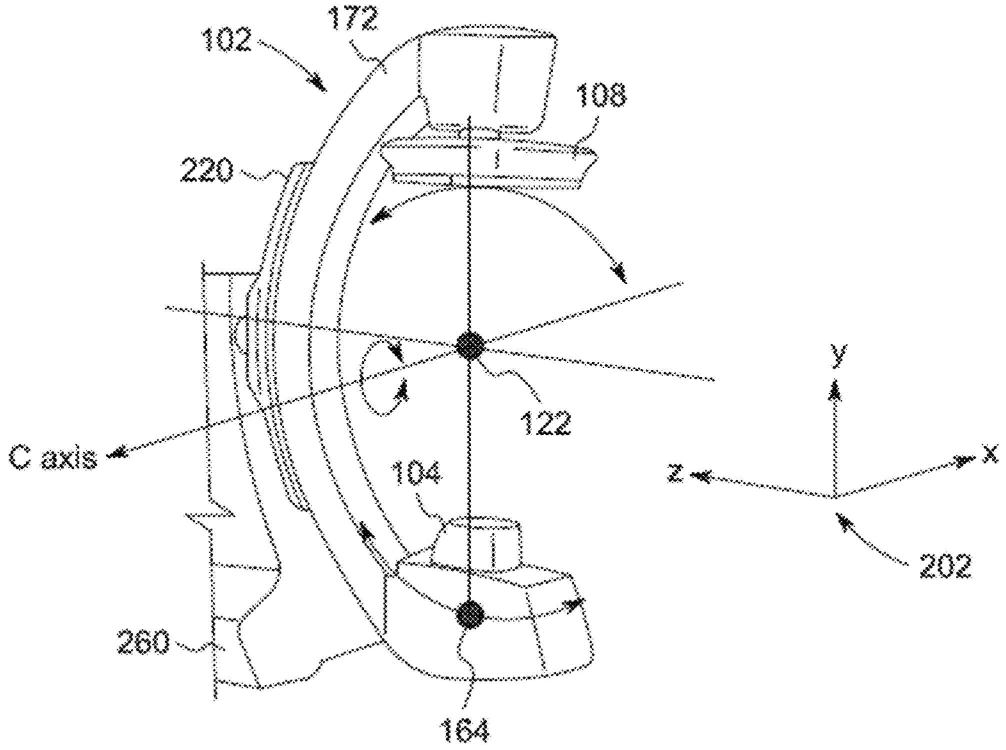
FIG. 6 schematically illustrates another of the axes about which the C-arm can rotate, specifically depicting the C axis.

The C-arm 172 may be slidably coupled to the gantry mount 220 so that the C-arm 172 may be rotated about a C axis, as further described with reference to FIG. 6. The gantry mount 220 may be coupled to the movable station 260 in such a way that it may rotate about the P axis, as further described with reference to FIG. 5. During conditions in which the C-arm 172 is coupled to the gantry mount 220, when the gantry mount 220 rotates about the P axis, so does the C-arm 172, as seen in FIG. 5

The C-arm 172 may be constructed in a partially-circular or partially-ovular shape where the signal transmitter 104 may be mounted to one side of the C-arm 172 while the detector 108 may be mounted to the opposite side of the C-arm 172. In some examples, the signal transmitter 104 may be nearer to the floor than the detector 108, as seen in FIG. 2. When rotated along either the P or the C axis, these relative positions of the signal transmitter 104 and detector 108 may change, though the signal transmitter 104 and the detector 108 may always be opposite each other.

As explained previously, the signal transmitter 104 may transmit the beam of radiation 106 for receipt by the detector 108. The beam of radiation 106 may extend from the signal transmitter 104 to the detector 108 and the subject 112 may be positioned between the signal transmitter 104 and the detector 108 in such a manner that the beam of radiation 106 passes through a relevant portion of the subject 112. In embodiments in which the imaging system 100 is a CBCT, the beam of radiation 106 may be a cone beam, as previously described. The table 114 upon which the subject 112 rests may be moved about the floor of the room in order to position the subject 112 between the signal transmitter 104 and the detector 108.

In some examples, the imaging system 100 is a multi-modality x-ray imaging system which can be used during surgery. Imaging modalities may include, but are not limited to, fluoroscopy, 2-D (two dimensional) Radiography, and Cone-beam CT. Fluoroscopy is a medical imaging technique that shows a continuous x-ray image on a monitor, much like an x-ray movie. 2-D Radiography is an imaging technique that uses x-rays to view the internal structure of a non-uniformly composed and opaque object such as the human body. CBCT (cone beam 3-D imaging or cone beam computed tomography) also referred to as C-arm CT, is a medical imaging technique comprising x-ray computed tomography where the x-rays are divergent, forming a cone. Magnetic resonance imaging (MRI) may also be employed, with suitable precautions for using powerful magnets and controlling the magnetic fields they generate. In one embodiment, the imaging system 100 herein described may be a CBCT.

The present discussion of a CT imaging modality is provided merely as an example of one suitable imaging modality. For example, a CT system in a C-arm configuration, such as the system depicted in FIGS. 1 and 2, includes a signal transmitter and a detector mounted opposite to each other on the ends of a substantially C-shaped or semi-circular gantry, or C-arm, thereby defining an imaging plane with an isocenter 122. It will be recognized that in other imaging systems within the present disclosure, one of the signal transmitter or detector may remain in a fixed position while the other of the source or detector is movable with respect to the patient. During an image acquisition, the C-arm may rotate the signal transmitter and the detector about an axis of rotation, which may coincide with the isocenter 122.

The movable station 260 may include the gantry motor controller 130 which may serve a dual operational function of (1) controlling the movement of the omni-directional wheels on the gantry mount 220 and the rotatable gantry 102 to position the signal transmitter 104 in relation to the subject 112, and other component movements as needed, and (2) controlling imaging functions for imaging the subject 112 once proper positioning has been achieved.

The beam of radiation 106 may have the focal point 164 (e.g., a source) at a vertex end 280 of the cone, which is at the side of the C-arm 172 where the signal transmitter 104 may be located. The base end 282 of the cone-shaped beam of radiation 106 may be opposite the focal point 164, insofar that it may be at the side of the C-arm 172 where the detector 108 may be located. As previously described, the detector 108 may comprise multiple detector elements 128 that together sense the beam of radiation 106.

The C-arm 172 may be rotated about one or more rotational axes to provide a large range of motion in the six degrees of freedom (DOF) described below. Under the control of the system controller 126, there are two main modes of motion: positioning of the movable station 260 and positioning of the rotatable gantry 102. Other positioning modes are described and may also be included.

The wheels (not pictured) may allow the movable station 260 to be positioned in all three DOF about the horizontal plane (X, L, Z). "L" is an imaging system 100 rotation about the vertical Y axis of coordinate system 202. "X" is a system forward and backward positioning along the X-axis of coordinate system 202, and "Z" is a system of lateral motion along the Z-axis of coordinate system 202. Under the control of the system controller 126, the imaging system 100 can be positioned in any combination of X, Y, and Z with unlimited range of motion.

The rotatable gantry 102 positioning may be accomplished about three axes, Y, P, and C. "Y" is rotatable gantry 102 vertical positioning. The P axis extends from the isocenter 122 towards the rotatable gantry 102 running parallel to the floor of the room. The C axis is perpendicular to the P axis and the C axis is parallel to the floor. The P axis and the C axis intersect at the isocenter 122.

Figure 3:
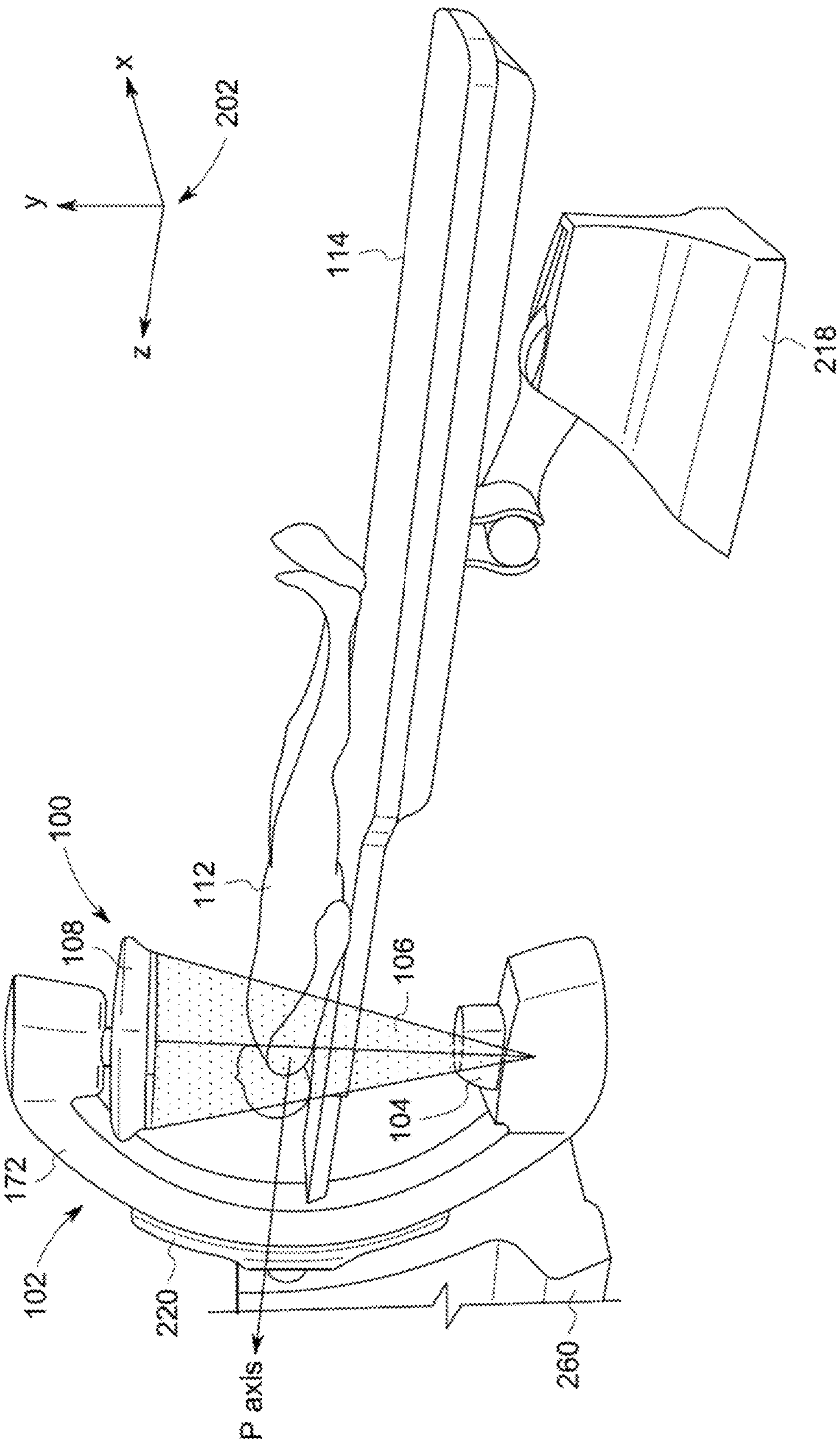
FIG. 3 shows the imaging system of FIG. 2 positioned about a subject from a “frontal” view.
Figure 4:
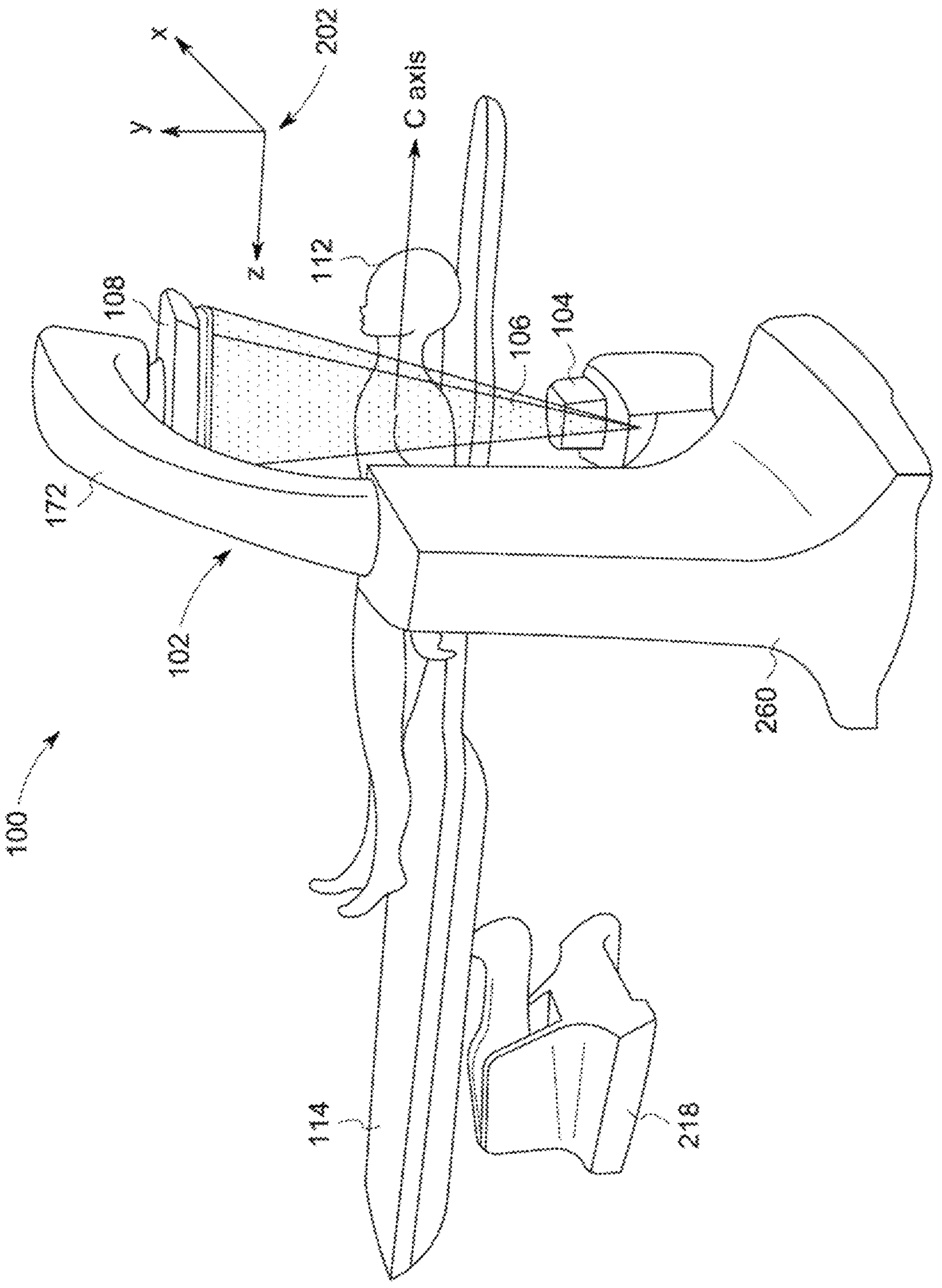
FIG. 4 shows the imaging system of FIG. 2 positioned about the subject from a “lateral” view.

Turning now to FIGS. 3-6, illustrations of multiple axes of rotation of the C-arm 172 are depicted. The C-arm 172 may be rotated about two separate axes, the P axis and the C axis. In one example, the gantry may be aligned in the "frontal" position, defined as the position where the P axis corresponds to the Z anatomical axis, as shown in FIG. 3. In another example, the gantry may be aligned in the "lateral" position, defined as the position where the C axis corresponds to the Z anatomical position, as shown in FIG. 4. The ability for different positions of the rotatable gantry 102 increases the range of options for the rotational trajectory of the rotatable gantry 102, thereby increasing the possibility of finding the optimal 3-D FOV which may in turn enable larger areas of intersection between the 3-D FOV and the target anatomy. Additionally or alternatively, the choice of positioning in either a frontal or a lateral position may depend on location of the region of interest. For example, a region of interest located in the pelvis of a subject may not be accessible with the gantry positioned in the frontal position and therefore positioning the gantry at the lateral position may be chosen. Also additionally or alternatively, ancillary equipment (such as a bedside ultrasound or respirator) may limit positioning of the gantry to either frontal or lateral. FIG. 5 particularly depicts the rotational trajectory of the C-arm around the P axis, as described above, and FIG. 6 particularly depicts rotational trajectory of the C-arm around the C axis, as described above.

Figure 7:
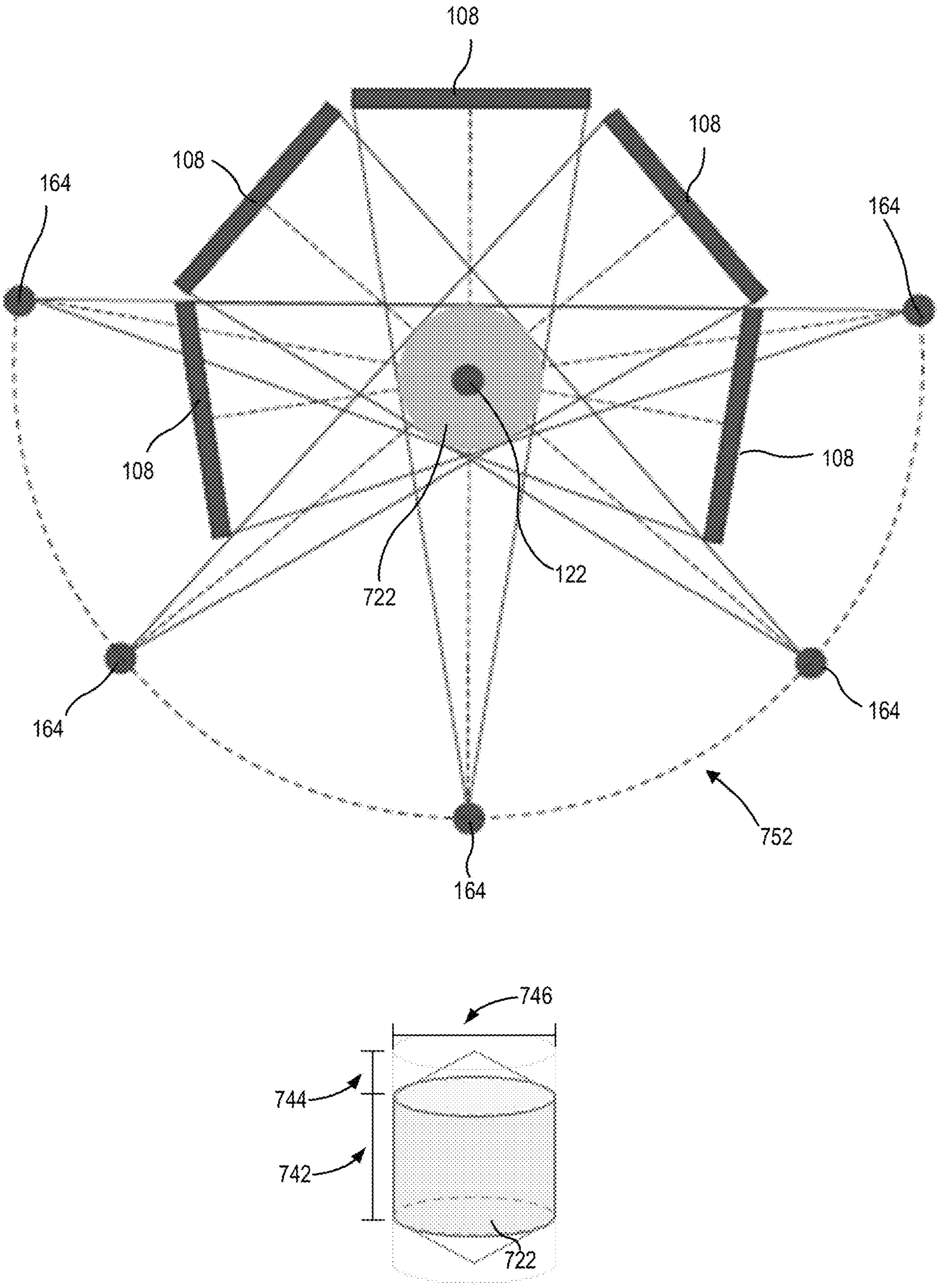
FIG. 7 schematically illustrates a rotational trajectory of the C-arm CBCT and the beam of radiation, including the computed 3-D field of view.

FIG. 7 schematically shows an example rotational trajectory 752 of the C-arm (e.g., C-arm 172). Image acquisition may occur as the C-arm 172 rotates about the subject 112, and one or more 2-D and/or 3-D images may be generated from the acquired detector data. The rotation of the rotatable gantry 102, including the rotation of the C-arm 172 and the beam of radiation 106, about one or more rotational axes (e.g., the P and C axes), may create a 3-D field of view (e.g., 3-D field of view 722) as the beam of radiation 106 rotates along the circular trajectory. In some examples, the 3-D field of view may be defined as the intersection of the x-ray cone beams throughout the rotation of the focal point 164 (e.g., the source of x-ray radiation). In some examples, the C-arm 172 may be rotated about only one axis such that the 3-D field of view is a cylinder with conical shaped extensions at the bases. In other examples, the C-arm may be rotated about more than one axis such that the 3-D field of view takes a shape that is rounder than a cylinder but is not as perfectly round as a sphere as based on variations in axis spin or detector to source distance. The shape of the detector 108 may also affect the shape of the 3-D field of view 722, for example a detector with a rounder shape may produce a 3-D field of view rounder than a cylinder which is produced with a rectangular shaped detector. Additionally, other trajectories may combine rotational and translational movement. An example of this may be the gantry being rotated about the patient while the distance between the source and the detector is continuously adjusted in order to avoid collisions. In this example, the resultant shape of the 3-D field of view may be an ellipse. In a second example, the isocenter could be continuously varied either by translating the gantry (and thus the isocenter) or by translating the patient. In this second example, the resultant shape of the 3-D field of view may also be an ellipse. The figures included herein show examples where the C-arm 172 is rotated about only one axis for simplicity. Advantageously, 3-D imaging that creates a 3-D field of view may increase visualization of a patient's anatomy compared to 2-D imaging.

The extent of the imaging subject that may be imaged by the imaging system 100 may be directly dependent on the shape and size of the 3-D field of view 722. The relative position of the focal point 164, the detector 108, and the rotatable gantry 102, as well as a rotational trajectory 752 combine to determine the shape and size of the computed 3-D field of view 722. In this example, the C-arm 172 is being rotated about a single axis. The figure shows multiple snapshots of the positions of the focal point 164 (e.g., a source) and the detector 108 as the C-arm 172 (not pictured in FIG. 7) traverses different angular positions (e.g., rotates).

The closer the detector 108 is to the focal point 164, the wider the beam of radiation 106 may be and therefore the larger the 3-D field of view 722 may be. The distance between the detector 108 and the focal point 164 may be limited due to possible collisions of the components (e.g., the signal transmitter 104 and the detector 108) and the subject 112 or the table 114.

In an example, there may be constant geometry of all components, perfect circular rotational trajectory 752, and the cone beam of radiation 106 may be symmetrical. In the ideal example as described, there may be minimum source rotation angle for no missing data for tomographic reconstruction (e.g., 200 degrees of rotation of the C-arm 172). In such an example, if the C-arm 172 were rotated about a single axis, the computed 3-D field of view 722 would be a cylinder with conic extensions at the bases of which the two circular bases were perfect circles.

Figure 8:
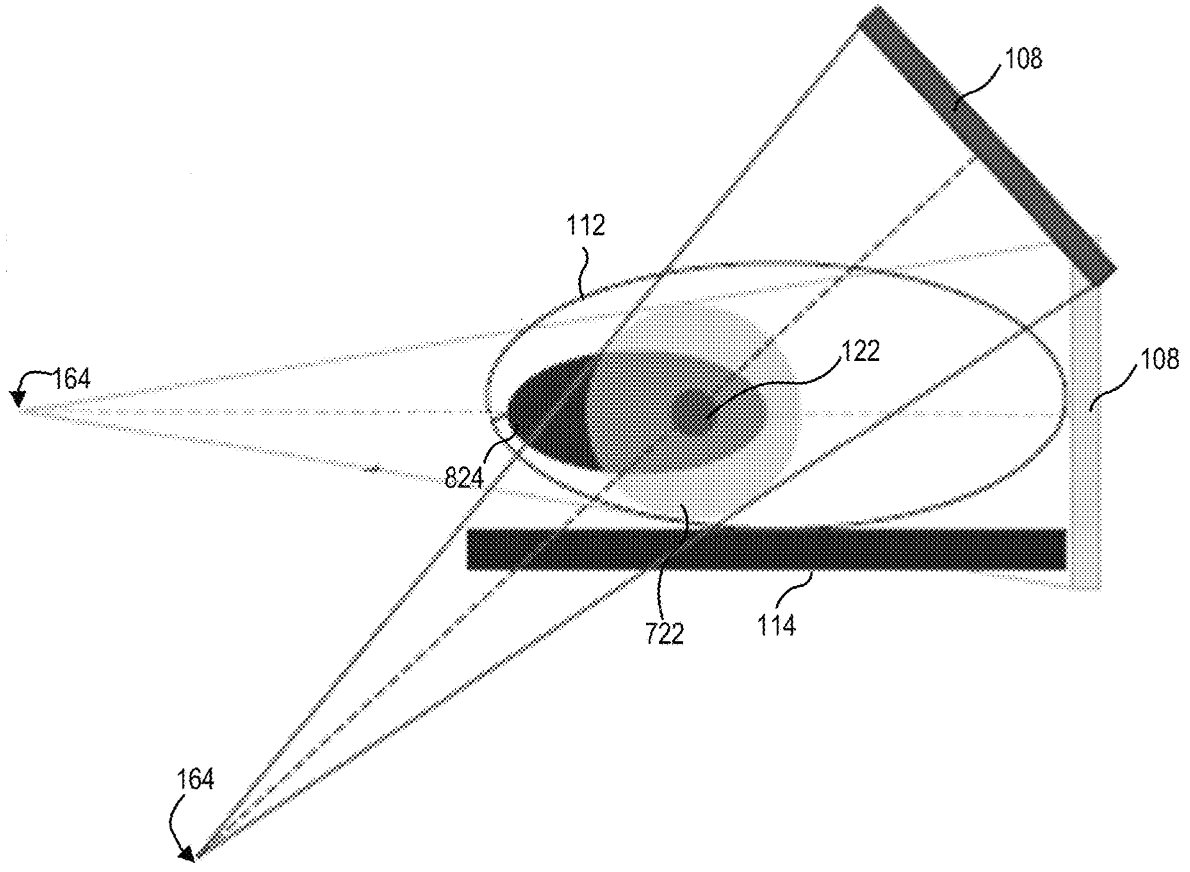
FIG. 8 schematically illustrates a sample 3-D field of view as it relates to a subject and a target anatomy.

FIG. 8 demonstrates an example of the intersection between the 3-D field of view 722 and the subject 112, including the intersection between the 3-D field of view 722 and a target anatomy 824 of the subject 112. For CBCT, the imaging FOV of the imaging system is relatively small and centered on the isocenter. In some instances, the target region of interest (ROI), which may be a particular organ, organ system, or object to be imaged (e.g., the target anatomy 824) may be off-center with respect to the subject 112. Therefore, the subject 112 may be positioned such that the field of view coincides with the target ROI. This process is described in greater detail below.

The field of view and image quality may be dependent, at least in part, upon the relative positions of components within the imaging system. As depicted in FIG. 7, these include a first distance between the source (e.g., the focal point 164) and the detector 108 (SID), a second distance between the source (e.g., the focal point 164) and the isocenter 122 (SOD), and a predicted exposed area (e.g., field of view) at the detector 108, which at its maximum is the diameter of the detector 108 (FOV). To increase the diameter of the 3-D field of view 722, one may decrease the SID (e.g., move the detector 108 and the signal transmitter 104 closer together). However, the patient's body, or other objects supporting the patient, the imaging system itself, and/or the arrangement of the imaging room may create further constraints on the positions of the signal transmitter 104 and the detector 108. This is particularly true if the target ROI (e.g., the target anatomy 824) is off-center with respect to a rotation axis about the patient, as depicted in FIG. 8. In embodiments as disclosed in further detail herein, an optimal or desired 3-D field of view (such as the 3-D field of view 722) with regard to image quality constraints may be computed prior to image acquisition, and the computed 3-D field of view may be represented as a virtual overlay in augmented reality that may be used to ideally position the subject 112. In this way, the intersection between the 3-D field of view 722 and region of interest may be visualized and adjusted prior to image acquisition.

However, the ideal case described above may be unlikely to occur due to imperfect geometry of the imaging system whereby the P axis and C axis may not intersect, the cone beam of radiation 106 may not be perfectly centered on the detector 108, the cone beam of radiation 106 may be asymmetric due to imperfect collimation, and/or the gantry mechanical structure may deform during rotation. These non-idealities may be accounted for by calibrating the geometry of the imaging system 100, thus allowing excellent cone beam reconstruction. Mechanical deformations may be reproducible, meaning that if a same motion trajectory is repeated, structural deformations (e.g., deviation from ideal geometry or a pure circular trajectory) may be the same. Hence, if the geometry of the system at each imaging position of the source and detector along the trajectory is known, deformations may be accounted for. Accounting for deformation may include use of a correction factor (e.g., constant proportional factor). However, this calibration may result in the actual 3-D field of view volume being smaller than the ideal 3-D field of view. Geometric calibration may entail imaging a known object (e.g., a calibration phantom) at each imaging position along the trajectory. Known features of the calibration phantom may be projected on the detector of the imaging system and the projection geometry of the imaging system may be mathematically derived from the known features detected in each image along the trajectory. A set of parameters may be calculated at each angular position and arranged into two matrices of intrinsic and extrinsic parameters. Intrinsic parameters may describe the imaging system geometry regardless of its position in the physical world and regardless of the imaged subject. Extrinsic parameters may describe the position and orientation of the imaging system. The calibration phantom may include a series of small opaque spheres located on a helical curve. This calibration process may assume that the table is in a fixed position or may account for various positions of the table.

The practical importance of a larger 3-D field of view is that the image provided may allow for larger intersection with the target anatomy 824 of the subject 112 (e.g., a patient). In FIG. 8, the table 114 has been positioned to center the subject 112 at the limit of a detector collision situation to maximize the intersection between the 3-D field of view 722 and the target anatomy 824. In this example, if the table 114 were positioned any further towards the detector 108 in order to move the target anatomy 824 into greater intersection with the 3-D field of view, the detector 108 would collide with the table 114 and/or the subject 112 during C-arm 172 rotation. Visualizing the position and size of the 3-D field of view 722 with respect to the subject 112 and the target anatomy 824 is a solution to simplifying the positioning process.

Figure 9:
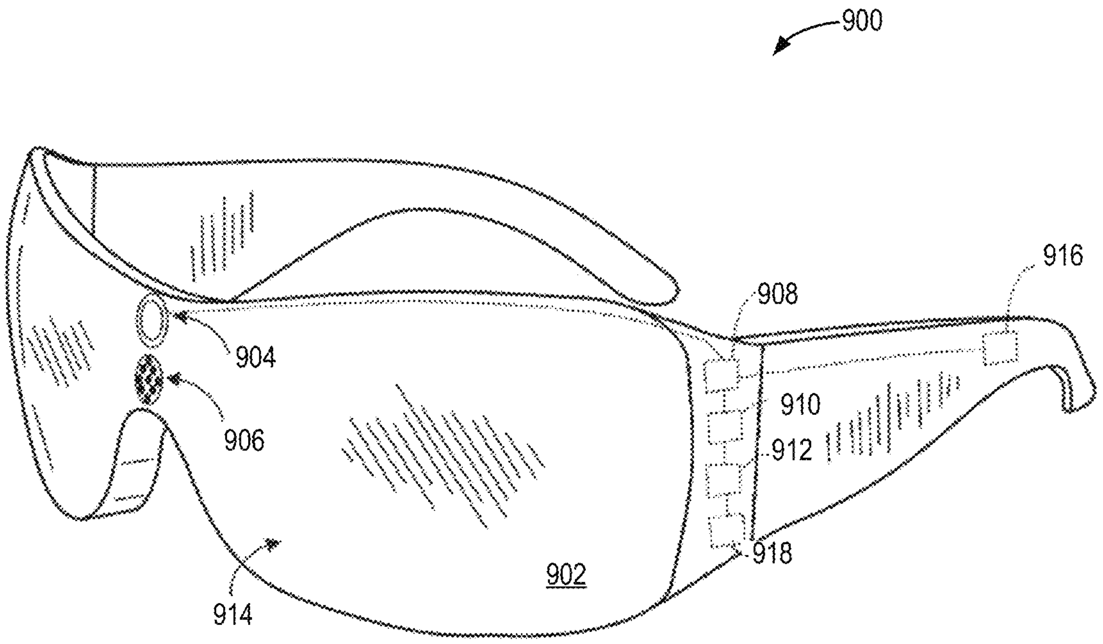
FIG. 9 depicts an illustration of an example augmented reality (AR device).
Figure 10:
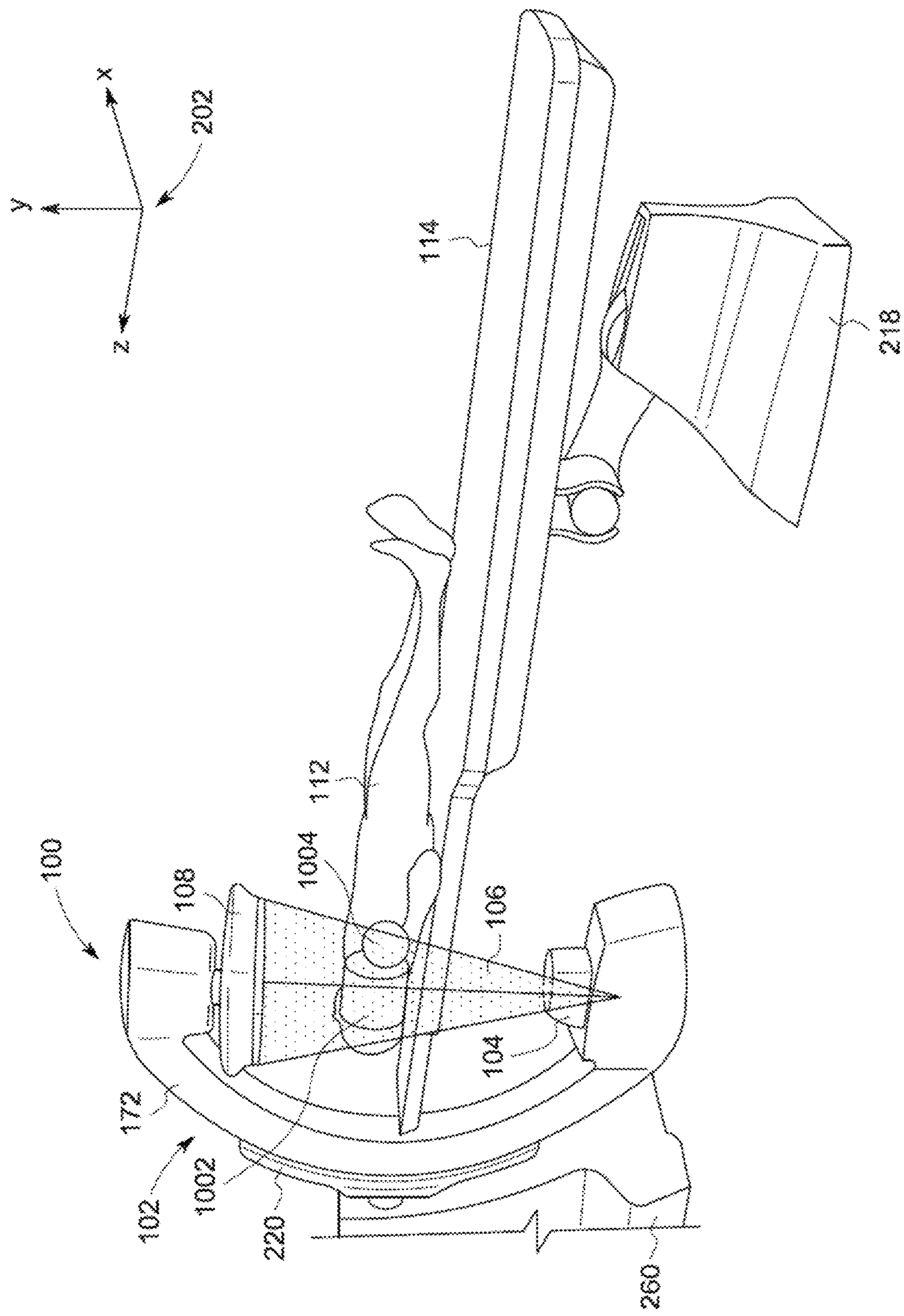
FIG. 10 shows the imaging system of FIG. 2, the beam of radiation, the target anatomy, and the virtual 3-D field of view as it may be viewed through an AR device.
Figure 11:
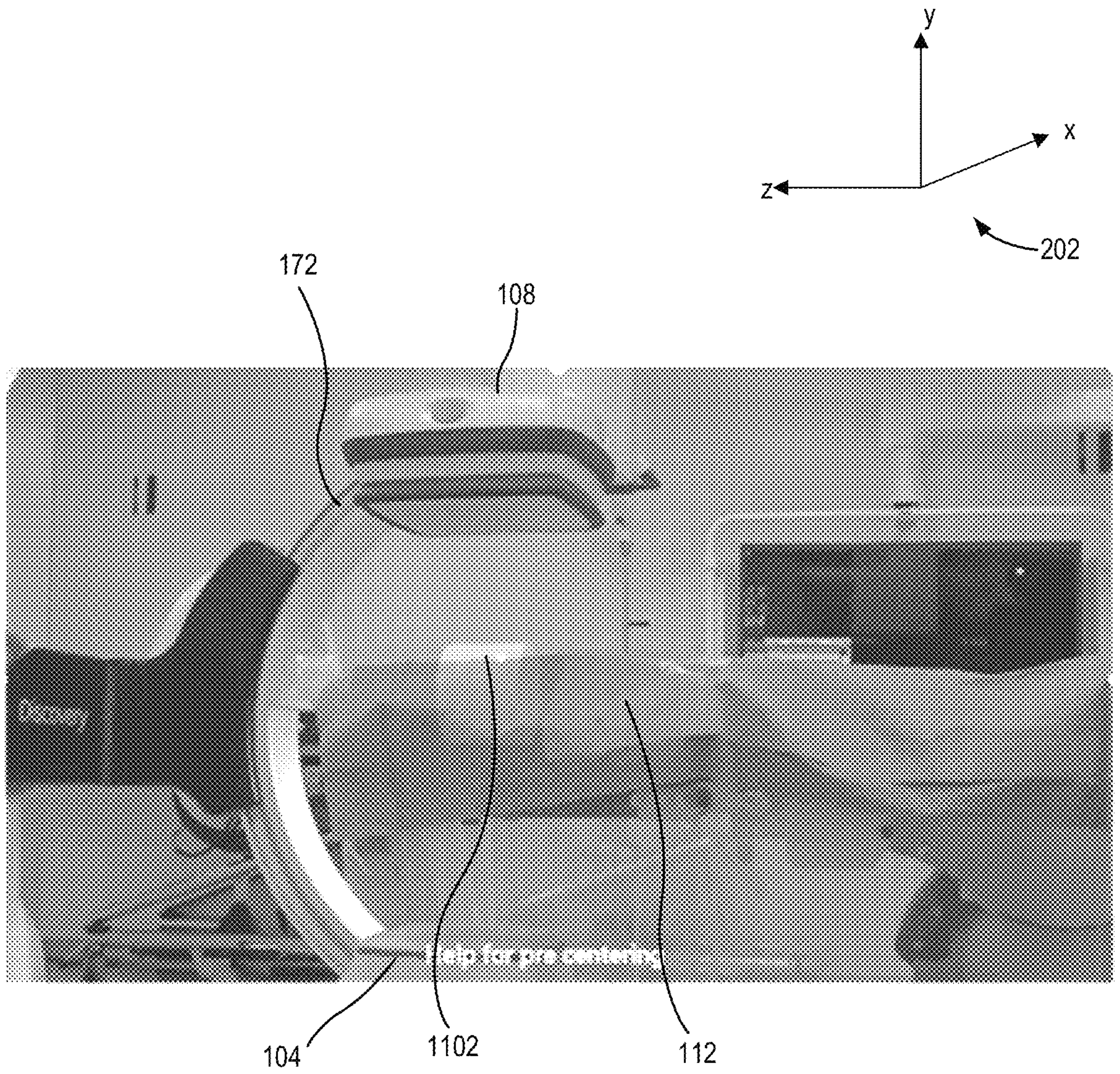
FIG. 11 shows an example display output of the AR device.
Figure 12:
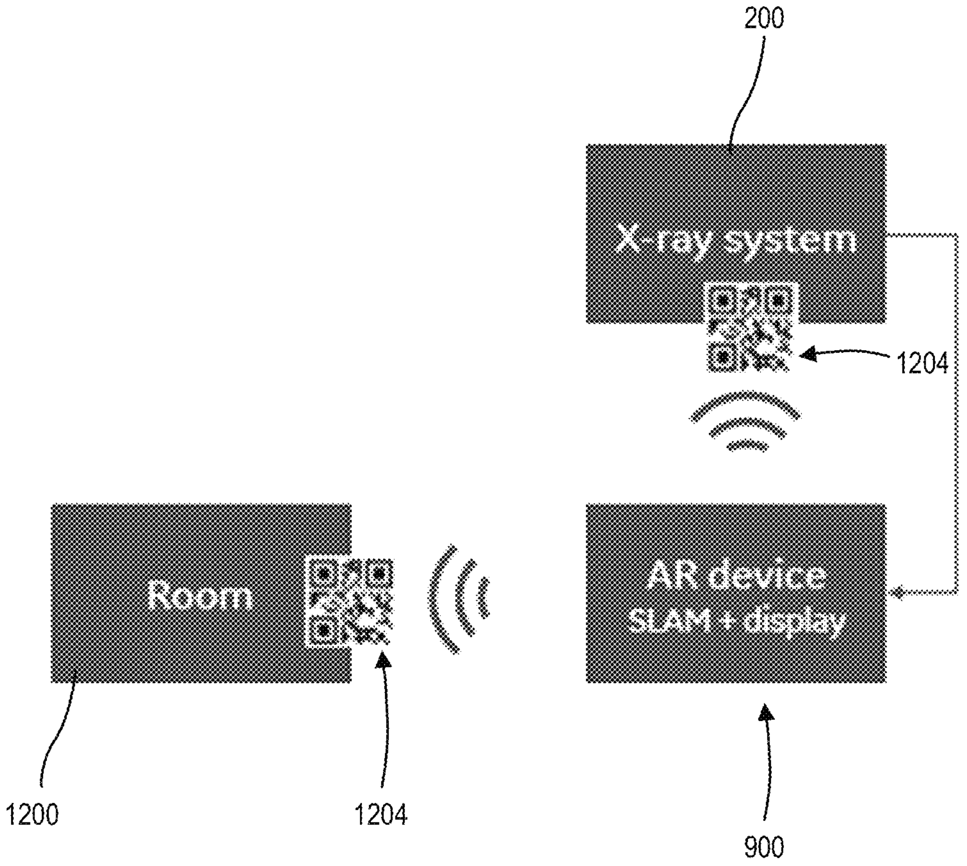
FIG. 12 is a block diagram of the room housing the imaging system AR device.

Embodiments of an AR system are now described with reference to FIGS. 9 through 12 and which may be used with the imaging system shown in FIGS. 1 through 8. FIG. 9 depicts an example of an AR device 900 while FIGS. 10 through 12 depict examples of visual outputs of the AR device 900 as well as localization aide with optional markers. The AR device 900 may enable a user who is using the AR device 900 to visually observe graphical objects that are displayed as an overlay to illustrate a computed 3-D field of view (e.g., 3-D field of view 722) as a virtual object in the AR space as well as, in some examples, an overlay of a target anatomy (e.g., target anatomy 824) if data of the target anatomy is available to the AR device 900. The AR device is shown herein as being in the form of a headset, but it is appreciated that the AR device could take on other forms without departing from the scope of this disclosure, such as a smartphone or tablet.

FIG. 9 shows an example of an external computing device, such as an AR device 900, that may be worn by a user (not pictured) to visualize a graphical representation of a computed 3-D field of view (such as 3-D field of view 722) as computed by the imaging system 100. AR device 900 may include a transparent display 914. It will be appreciated that in other examples, AR device 900 may take other suitable forms in which a transparent, semi-transparent or non-transparent display is supported in front of the patient's eye or eyes. Additionally, many other types and configurations of display devices having various form factors may also be used within the scope of the present disclosure. Such display devices may include, but are not limited to, hand-held smart phones, tablet computers, and other suitable display devices. In this example, AR device 900 may include a display system 918 and transparent display 914 that enables images such as holographic objects to be delivered to the eyes of a wearer (not pictured). The transparent display 914 may be configured to visually augment an appearance of an environment or a room including one or more physical objects (e.g., 3-D field of view 722), to the user viewing the environment or room through the transparent display 914. For example, the appearance of the room may be augmented by graphical content (e.g., one or more pixels each having a respective color and brightness) that is presented via the transparent display 914 to create a mixed reality environment.

The transparent display 914 may also be configured to enable the user to view a physical, real-world object in the environment through one or more partially transparent pixels that are displaying a virtual object representation. In one example, the transparent display 914 may include image-producing elements located within lenses 902 (such as, for example, a see-through Organic Light-Emitting Diode (OLED) display). As another example, the transparent display 914 may include a light modulator on an edge of the lenses 902. In this example the lenses 902 may serve as a light guide for delivering light from a light modulator to the eyes of the patient. Such a light guide may enable a patient to perceive a holographic image located within a physical environment that the patient is viewing, while also allowing the patient to view physical objects in the physical environment, thus creating a mixed reality environment.

As another example, the transparent display 914 may include one or more opacity layers in which blocking images may be generated. The one or more opacity layers may selectively block real-world light received from the environment before the light reaches an eye of the user wearing AR device 900. By selectively blocking real-world light, the one or more opacity layers may enhance the visual contrast between a virtual object and the physical environment within which the virtual object is perceived by the patient.

AR device 900 may also include various sensors and related systems. For example, AR device 900 may include an eye-tracking sensor system that utilizes at least one inward facing sensor 906. The inward facing sensor 906 may be an image sensor that is configured to acquire image data in the form of eye-tracking information from a user's eyes. An eye-tracking sensor system may then use this information to track a position and/or movement of the user's eyes.

AR device 900 may also include sensor systems that receive physical environment data from the environment. For example, AR device 900 may include an optical sensor system that utilizes at least one outward facing sensor 904, such as an optical sensor. Outward facing sensor 904 may detect movements within its field of view, such as gesture-based inputs or other movements performed by the user (not pictured) or by a person or physical object within the field of view. Outward facing sensor 904 may also capture two-dimensional image information and depth information from the environment and physical objects within the environment. For example, outward facing sensor 904 may include a depth camera, a visible light camera, an infrared light camera, and/or a position tracking camera. Outward facing sensor 904 may also capture images of the environment or the room in which the wearer of the device (e.g., the user) is situated. In one example, a mixed reality display program may include a modeling system that uses such input to generate a virtual environment that models the physical environment surrounding the user In some examples, AR device 900 may be configured to generate an augmented reality display where the virtual objects described herein are overlaid with the environment captured with the outward facing sensor 904. This display may be sent to a device of a remote operator and used by the remote operator to guide the actions of a local operator in the room, control the imaging system movement from a remote location, and/or provide guidance to the patient (position arms, hold breath).

AR device 900 may include depth sensing via one or more depth cameras. In one example, each depth camera may include left and right cameras of a stereoscopic vision system. Time-resolved images from one or more of these depth cameras may be registered to each other and/or to images from another optical sensor such as a visible spectrum camera, and may be combined to yield depth-resolved video. In other examples a structured light depth camera may be configured to project a structured infrared illumination, and to image the illumination reflected from a scene onto which the illumination is projected. A depth map of the scene may be constructed based on spacings between adjacent features in the various regions of an imaged scene. In still other examples, a depth camera may take the form of a time-of-flight depth camera configured to project a pulsed infrared illumination onto a scene and detect the illumination reflected from the scene. It will be appreciated that any other suitable depth camera may be used within the scope of the present disclosure.

AR device 900 may also include a position sensor system that utilizes one or more motion sensors 910 to enable motion detection, position tracking, and/or orientation sensing of the AR device 900. For example, a position sensor system may be utilized to determine a direction, velocity, and acceleration of the user's head. A position sensor system may also be utilized to determine a head pose orientation of the user's head. In one example, a position sensor system may comprise an inertial measurement unit configured as a six-axis or six-degree of freedom position sensor system. This example position sensor system may, for example, include three accelerometers and three gyroscopes to indicate or measure a change in location of AR device 900 within three-dimensional space along three orthogonal axes (e.g., x, y, z), and a change in an orientation of AR device 900 about the three orthogonal axes (e.g., roll, pitch, yaw). A position sensor system may also support other suitable positioning techniques, such as GPS or other global navigation systems. Further, while specific examples of position sensor systems have been described, it will be appreciated that other suitable position sensor systems may be used.

In some examples, motion sensors 910 may also be employed as user input devices, such that a user may interact with AR device 900 via gestures of the neck and head, or even of the body. AR device 900 may also include a microphone system that includes one or more microphones 908. Further, audio may be presented to the user via one or more speakers 916.

AR device 900 may also include a controller 912 having a processor and memory that are in communication with the various sensors and systems of AR device 900. In one example, the memory may include instructions that are executable by the processor to receive signal inputs from the sensors and forward such inputs to a processor of the AR device 900 (or another processor on an external device) (in unprocessed or processed form), and to present display content (e.g., images) to the user via the transparent display 914. AR device 900 may be equipped with computer programming and memory to compute SLAM (Simultaneous Localization and Mapping) algorithms which may use the signal inputs from the sensors and cameras, as described, to localize the AR device within the environment with relation to other objects visualized by the sensors and cameras (e.g., the imaging system 100).

It will be appreciated that AR device 900 and related sensors and other components described above are provided by way of example. These examples are not intended to be limiting in any manner, as any other suitable sensors, components, and/or combination of sensors and components may be utilized. Therefore it is to be understood that AR device 900 may include additional and/or alternative sensors, cameras, microphones, input devices, output devices, etc., without departing from the scope of this disclosure. Further, the physical configuration of AR device 900 and its various sensors and subcomponents may take a variety of different forms without departing from the scope of this disclosure. For example, rather than including a transparent display, AR device 900 may include a standard light-blocking display, and may present a view of the physical environment via a video feed obtained from outward facing sensor 904. A mixed reality experience may be provided by AR device 900 by including additional display content (e.g., virtual objects) incorporated in or overlaid on the video feed. In still further examples, AR device 900 may be a virtual reality device configured to provide a fully virtual experience by displaying display content on the light-blocking display that does not include a real-time view of the physical environment.

Although some operational embodiments are discussed in the context of an AR system that displays graphics on a see-through display screen of an AR headset, the disclosed operations may additionally or alternatively be used to display graphics on other types of display screens, such as other displays mounted elsewhere in an operating room.

FIG. 10 illustrates an example display view of the AR device 900, depicting what may be visualized through the AR device 900 before image acquisition. In this illustration, a virtual 3-D field of view 1002 is depicted as a cylinder within the imaging system reference frame about the isocenter 122. In FIG. 10, a virtual target anatomy 1004 is depicted as a sphere within the patient. The AR device 900 may allow for visualization of the virtual 3-D field of view 1002 and optionally the virtual target anatomy 1004 and as such may allow the user to visualize the graphical objects and their relative positions in relation to the subject 112 during patient positioning. In the example shown in FIG. 10, the virtual 3-D field of view 1002 may be offset from the target anatomy 1004, and thus a user may reposition the table 114 to align the virtual 3-D field of view 1002 and the target anatomy 1004. Alternatively or additionally, a user may reposition the rotatable gantry 102 of the imaging system 100 to align the virtual 3-D field of view 1002 and the virtual target anatomy 1004.

FIG. 11 is a demonstration of what the user of the AR device may visualize through the AR device 900 when the AR device 900 is displaying the virtual 3-D field of view as a virtual object. In this figure, the positions of a virtual 3-D field of view 1102, the C-arm 172, the subject 112, the signal transmitter 104, and the detector 108 are shown in relation to each other as they would be visualized through the AR device 900. As depicted, the user of the AR device 900 may visualize both the graphical objects it is displaying as well as the physical objects in the environment through the AR device 900. As such, the user may visualize the rotatable gantry 102, the subject 112, the table 114, and the virtual 3-D field of view 1102, all in their relative positions within the room reference frame (and the imaging system reference frame).

When setting up the imaging system 100 for use, the C-arm 172 to which the signal transmitter 104 and detector 108 are mounted, may come in from a frontal or lateral view, as described above. There may be other arrangements of position for the C-arm 172 and the rotatable gantry 102. Then, during an imaging scan, the C-arm 172 rotates along the rotational trajectory 752 about the isocenter 122, where the subject 112 may reside on table 114. Predictive visualization and CBCT centering can be beneficially used during setup in order to reduce potential collisions with either the subject 112 or the table 114 and to reduce the number of scans taken which in turn may reduce the radiation exposure to the subject 112 as well as medical staff in the room. The AR device 900 may enable a user, without operationally starting an imaging scan, to visualize if the computed 3-D field of view 722 intersects with the target anatomy 824, which may further reduce the number of required scans in order to visualize the target anatomy 824.

FIG. 12 demonstrates three of the four different reference frames of such a method. In one embodiment there may be four different reference frames: 1) the room 1200 in which the imaging system 100, the subject 112, and the AR device 900 reside, 2) the imaging system 100 (including the rotatable gantry 102 and the table 114), 3) the AR device 900, and 4) the subject 112. The imaging system 100 may be located in the room reference frame (e.g., because the table 114 is in face sharing contact with the floor of the room 1200 at a given point and the rotatable gantry 102 is in face sharing contact with the floor of the room 1200 at a given point). All movable parts of the imaging system 100 can be localized in the imaging system reference frame in real time, as described above, where all angles and translations are known and the envelope of fixed and movable parts is also modeled to a certain accuracy for collision management purposes. The geometry of all the parts of the imaging system reference frame may be known by the imaging system 100 and therefore the imaging system may be able to calculate, via computer readable instructions stored in the non-transitory memory of the imaging system 100, the 3-D field of view 722.

The calculation of the rotational trajectory 752 and the size and position of the 3-D field of view 722 may be completed by the imaging system 100 based on known geometric parameters. The imaging system 100 may know the relative position of the detector 108 and the signal transmitter 104 and consequently the position of the focal point 164 (e.g., the source). It may then be able to calculate a first distance between the detector 108 and the focal point 164 as well as a second distance from the focal point 164 to the isocenter 122. The imaging system 100 may also know the diameter of the detector 108 that may be exposed to the beam of radiation 106. The values herein (the first distance from the focal point 164 to the detector 108, the second distance from the focal point 164 to the isocenter, and the diameter of the exposed field of view at the detector 108) may be used to calculate a diameter 746 of the resultant 3-D field of view 722 as the source (e.g., the focal point 164) traverses along the rotational trajectory 752, as shown in FIG. 7 and as previously described with reference to FIG. 8. The resultant 3-D field of view 722 may be a cylinder with conical extensions at each base of the cylinder. The calculated diameter 746 of the 3-D field of view 722 may then be used to calculate the total volume of the 3-D field of view 722 by finding the area of the base of the cylinder (diving the diameter in half to find the radius, squaring the radius and then multiplying by pi) and multiplying by a height 742 of the cylinder (in this example, the height 742 of the cylinder is defined by the predicted width of the cone beam at the intersection of all positions as the imaging system 100 rotates minus a height 744 included in each of the conical extensions). As described above, the 3-D field of view may also include conical extensions, the volume of which may be found by squaring a radius of a base of one cone (the radius of the base is equal to the radius of the cylinder), multiplying by pi, and multiplying by a third of the height 744 of the cone. The height 744 of the cone may be defined by the intersection of the angular edge of the cone beams as they are rotated around an axis. The total volume of the two cones may be found by multiplying the volume of one cone by two. The total volume of the 3-D field of view may be found by adding the volume of the cylinder and the volume of the two cones.

In some examples in which the 3-D field of view 722 is not a cylinder with conical extensions, such as when translations are employed and the 3-D field of view provided is an ellipse, a different calculation may be performed. Additionally, in any shape of the 3-D field of view, a correction factor may be used as a part of the calculation in order to correct for non-isocentricities. In one example, the correction factor may be 0.95 and may account for factors such as deformation and x-ray beam misalignment.

The imaging system 100 may also compute where an exposed area on the detector 108 will be for each position along the rotational trajectory. This may allow for acquisition of a larger 3-D field of view as compared to taking smaller sized projections. The geometry and the first location of the 3-D field of view 722 may be precisely defined, including the effect of deformations, and can be sent to the AR device 900.

AR devices, such as the AR device 900, may be equipped with a localization mechanism as described above. Said localization method, such as the process called SLAM, may allow for the AR device 900 to locate itself using its plurality of sensors and cameras by building a map of the environment (e.g., the room 1200). The AR device 900 may then identify, recognize, and locate references points to build a map of the environment.

A localization process of the AR device 900 may be performed in a number of ways. In a first method, the AR device 900 may have knowledge of a particular feature of the room and/or imaging system 100 (e.g., it may be provided location data of the imaging system and other equipment in the room to define specific locations of those components). The AR device may also know the specific location of itself within the room 1200, and may be able to relate its own position to the known positions of the other equipment in the room. With this information, the AR device can calculate the geometric transformation that relates the AR reference frame to the room reference frame and/or the imaging system reference frame in order to display graphical objects in the correct location within the imaging system reference frame.

In a second method, using its forward facing sensors and/or cameras, the AR device 900 may be able to determine the relative location of equipment in the room 1200 (e.g., the imaging system 100) with relation to its own relative positioning. Thus, the AR device 900 may locate the relative positions of itself and the other equipment (e.g., the imaging system 100) in the room 1200. The AR device 900 may repeatedly update the relative locations as the AR device 900, and consequently the sensors and cameras of the AR device 900, is moved about the room 1200. The AR device 900 may be sent data or information of the position of the imaging system reference frame with respect to the imaging system 100. The AR device 900, once it determines the relative position of the imaging system with respect to its own relative position, may be able to display graphical overlays in the correct position with respect to the imaging system 100 because the AR device 900 knows the relative positioning of the imaging system 100 in the room 1200 and the position of the imaging system reference frame within the imaging system 100.

Alternatively or additionally, navigation markers (e.g., QR codes), such as navigation markers 1204 may be placed at specific locations in the room (e.g., in face sharing contact with the walls of the room or other equipment in the room) and/or in face sharing contact with the imaging system 100 for localization, as shown in FIG. 12. The AR device 900 may sense the navigation markers 1204 via the outward facing sensors and cameras of the AR device 900 in order to build a map of the environment and the relative positions of the navigation markers 1204 and the equipment on which the navigation markers 1204 are placed.

The data of the computed 3-D field of view 722, indicating its relative position (e.g., the first position of the 3-D field of view) within the imaging system reference frame, may be sent to the AR device 900 in order for the AR device 900 to display a graphical object (e.g., a virtual representation of the 3-D field of view 722) that corresponds to the computed 3-D field of view 722. The AR device 900, using the self-localization method described above, may then be able to display the 3-D field of view 722 as a graphical object within the imaging system reference frame.

Being able to visualize a virtual representation of the 3-D field of view 722 may reduce risk of collisions between the subject 112 and the rotatable gantry 102 (including the C-arm 172, the signal transmitter 104, and the detector 108). Because the user may no longer use a trial-and-error system of positioning the subject 112 and the imaging system 100 in order to capture an image of the target anatomy 824, the subject 112 (e.g., a patient) and the other staff in the room may be exposed to a lesser amount of x-ray radiation. Additionally, visualization of a virtual representation of the 3-D field of view 722 may reduce the amount of time spent positioning the subject 112 and the imaging system 100 components (e.g., the rotatable gantry 102).

In all the description above, both the imaging system 100 and the AR device 900 have no knowledge of the subject 112 (e.g., the position of the subject 112 on the table 114 or the position of the target anatomy 824 within the subject 112). The process described above may allow a stereoscopic rendering of the 3-D field of view 722 to be viewed as a virtual object located inside the subject 112 at the first location with respect to the imaging system reference frame. The operator may position the subject 112 prior to the CBCT image acquisition (e.g., prior to the C-arm rotation) so that the virtual 3-D field of view object is located at a target location within the subject 112. Without direct visualization of the exact position of the target anatomy 824, this process may be completed based on user approximations of a second location of the target anatomy (e.g., if attempting to image the liver, the user may move the table in order to position the patient's right upper abdomen within the virtual 3-D field of view). This method is inherently suboptimal as it may lead to incomplete imaging of the target anatomy.

Additional virtual features may be displayed by the AR device 900 to aid in avoiding possible collisions between the rotatable imaging system and the patient. For example, the trajectory of the detector 108 or signal transmitter 104 may be displayed as a graphical object (e.g., a virtual rotational volume) by the AR device 900. This virtual rotational volume, called "3-D tunnel", may be a cylinder that gives the limit of the collision free volume (practically speaking this is the cylinder tangent to the detector surface along the rotational trajectory). If the 3D tunnel intersects anything (patient, stationary part of the system, ancillary equipment), an operator may be made aware that collisions will happen. A more sophisticated approach can be taken by modeling the entire volume "swept" by the gantry during rotation. If the AR device 900 receives an entire description of the geometry, it can render intersections of various volumes and therefore depict areas of collisions, for example as red graphic objects. In addition, recommendations to clear collision can be fed in the AR device 900 using textual information or graphics. The accuracy of the process of positioning the patient within the "3-D tunnel" may be inherently limited and may turn impractical in some situations because of patient surgical draping and inability to properly line up the subject 112 so that the target anatomy 824 is fully (or as near to fully as is possible with image quality constraints) imaged.

Anatomy localization and registration within the subject frame may be achieved in various manners. In one example, provided the subject 112 has not significantly moved, the coordinates of the target anatomy 824 may be determined from previously acquired images acquired by the imaging system 100. In this method, at least two planar (e.g., 2-D) images (e.g., intraoperative fluoroscopic x-ray images) may be acquired of the subject 112 by the imaging system 100 with the subject 112 in a particular position within the imaging system reference frame. Each of the 2-D x-ray images may be taken at a different angle. The user may define points within each of the 2-D x-ray images that correspond to a particular anatomical location or feature (e.g., the same target anatomy 824). These images may then define a coordinate plane of the patient and the imaging system 100 may convert the points of each of the 2-D x-ray images into a 3-D coordinate point in the coordinate plane. The imaging system 100 may calculate the coordinate point corresponding to the position of the target anatomy 824 within the subject 112 in the imaging system reference frame. The imaging system 100 may then send the data of the coordinate point (the data may include the positioning of the point within the 3-D coordinate plane and within the imaging system reference frame) to the AR device 900 for display and visualization. The virtual coordinate point that is displayed by the AR device 900 may be displayed as a sphere.

The coordinate point may be fixed within the imaging system reference frame with relation to the table 114 but movable within the imaging system reference frame with relation to the rotatable gantry 102 and C-arm 172. Then, the centering process may entail centering the target coordinate point within the virtual 3-D field of view 722 using the AR device 900. This centering process may be done by way of moving the table 114 (and as such, the subject 112 as he or she may be lying in direct contact with the table 114), taking into account limitations of movement of the table 114 to avoid collisions with the rotatable gantry 102 and the rotational trajectory 752. Alternatively, the user may move the rotatable gantry 102, taking into account limitations of movement of the rotatable gantry 102 to avoid collisions with the table 114. Given that the coordinate point is in a fixed position with relation to the table 114, the coordinate point may move in the AR visualized display the same as the table 114 is being moved (e.g., either manually or via the table motor controller 218). Additionally, given that the coordinate point is not fixed with relation to the rotatable gantry 102, when the rotatable gantry 102 is moved, the coordinate point may not move.

Alternatively, a 3-D imaging data set (e.g., a preoperative CT scan of a patient) may be used to develop an overlay of the target anatomy 824 for visualization in AR alongside the 3-D field of view 722. In one embodiment of this method, if a 3-D imaging data set (e.g., a preoperative CT scan) is available and a 2-D x-ray image has been taken by the imaging system (e.g., an intraoperative fluoroscopic image), the anatomy shown in the 3-D image may be registered to the x-ray image (e.g., an intraoperative fluoroscopic image). This then defines a coordinate transformation. This may all be done with reference to the imaging system reference frame so that the imaging system may know where the exact anatomy of the subject is (provided that the patient has not significantly moved from his/her position on the table in which the x-ray image was taken) with relation to the table 114 as part of the imaging system reference frame. The patient anatomy data set (as derived from the 3-D imaging data and registration to the 2-D x-ray image) may be fixed within the imaging system reference frame with relation to the table 114 but movable within the imaging system reference frame with relation to the rotatable gantry 102 and C-arm 172. If both this 3-D data set (in a segmented, simplified form) and registration data (the coordinate transformation) are sent by the imaging system 100 to the AR device 900, the anatomy (specifically the target anatomy 824) of the subject 112 that was registered can be visualized along with the 3-D field of view 722 at the correct location inside the subject 112. Positioning may then entail ensuring that the 3-D field of view 722 intersects with the target anatomy 824 as much as is allowable to avoid collisions. This centering process may be done by way of moving the table 114 (and as such, the subject 112 as he or she may be lying in direct contact with the table 114), taking into account limitations of movement of the table 114 to avoid collisions with the rotatable gantry 102 and the rotational trajectory 752. Alternatively, the user may move the rotatable gantry 102, taking into account limitations of movement of the rotatable gantry 102 to avoid collisions with the table 114. Given that the virtual patient anatomy is in a fixed position with relation to the table 114, the virtual patient anatomy may move in the AR visualized display the same as the table 114 is being moved (e.g., either manually or via the table motor controller 218). Additionally, given that the patient anatomy is not fixed with relation to the rotatable gantry 102, when the rotatable gantry 102 is moved, the virtual patient anatomy may not move. The overlay allows for positioning of the 3-D field of view at the correct location with respect to a target anatomy. The imaging system may be able to predict certain potential collisions because it knows the positions of the table and gantry and the gantry trajectory to a certain accuracy. If the imaging system predicts that the detector or signal transmitter may come into contact with the table during rotation of the gantry, rotation may be forbidden. Moreover, the imaging system may embed a patient envelop model which corresponds to an exclusion volume above the table to account for where the patient being imaged may be located. Thus, the system may be able to predict collisions both with the known elements of the imaging system itself (including the table), and it may predict potential collisions with body parts of the patient being imaged. Patient gender, height, weight, and BMI may be leveraged to enhance accuracy of the patient envelop model. Alternatively, a 95th percentile patient envelop model may be utilized rather than using specific patient data. Further, patient envelop information may be provided to the imaging system from the AR device 900, which may be able to sense the location, size, shape, etc., of the patient via its plurality of cameras and sensors.

The AR device 900, as previously described, may be able to determine relative location of the imaging system 100, including the position of the table 114. The overlay of the patient anatomy or the coordinate point (whichever option is chosen) may be viewed through an AR headset in the correct location because the AR device 900 has knowledge of the imaging system reference frame. As the table 114 is moved and/or rotated, so shall the overlay of the patient anatomy or the coordinate point (which may be visualized as a sphere) that was extrapolated from the 3-D data set (e.g., a preoperative CT scan) given that the table is part of the imaging system reference frame. In this way, the table 114 (and as such the subject 112) may be positioned to align the target anatomy 824 (visualized as either the coordinate point or the patient's anatomy) with the virtual 3-D field of view 722.

Displaying the computed 3-D field of view 722 alongside the subject 112's anatomy may provide additional ease of positioning of the subject 112. This may also allow for predictive visualization of the intersection between the image acquisition and the region of interest (e.g., the target anatomy 824). This method may reduce the amount of trial-and-error as well as increasing the efficiency of obtaining adequate image acquisitions.

Figure 13:
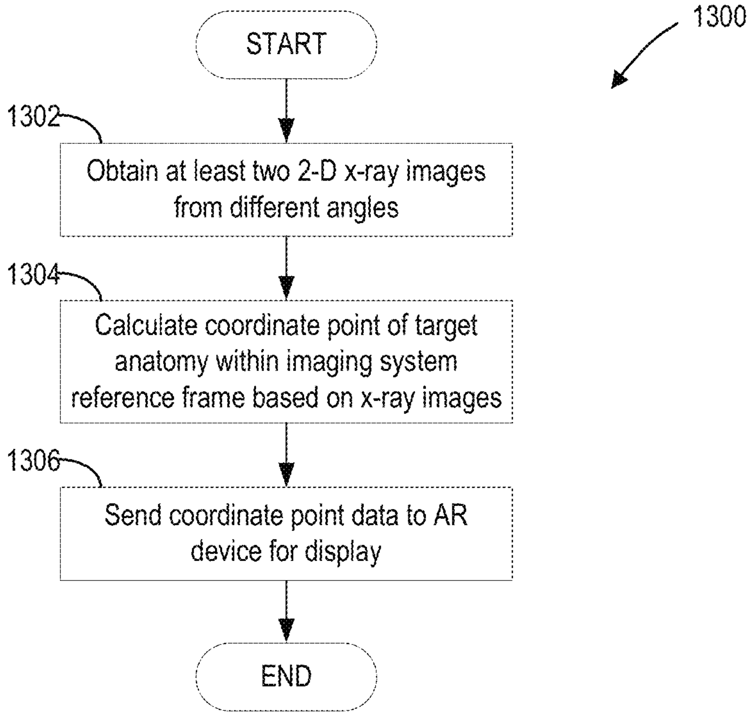
FIG. 13 is a flowchart depicting an example method for patient anatomy localization using 2-D data sets.

FIG. 13 is a flowchart that depicts a method 1300 for patient anatomy localization using a 2-D data set that may be optionally performed in conjunction with method 1500 in order for the imaging system to obtain data sets that may later be sent to the AR device. Method 1300 may be executed using computer readable instructions stored in the non-transitory memory of an imaging system (e.g., imaging system 100).

At 1302, at least two 2-D x-ray images (e.g., intraoperative fluoroscopic x-rays) may be obtained of a patient by an imaging system from at least two different angles within the imaging system reference frame. In one embodiment, there may be a coordinate system for the imaging system reference frame stored in the non-transitory memory of the imaging system. The 2-D x-ray images may be obtained by activating the x-ray source of the imaging system to project x-ray radiation towards the detector passing through a patient lying on a table in an operating room. Said patient may be positioned on a table such that a beam of radiation of the imaging system passes through and acquires x-ray data from relevant anatomy within the patient. At least two images (e.g., separate x-ray image acquisitions) may be taken with the x-ray source positioned at different locations for each of the x-ray image acquisitions to provide at least two views of the relevant anatomy from different angles. A point may then be defined in each of the 2-D x-ray images corresponding to the same position in the patient's anatomy.

At 1304, a coordinate point corresponding to the target anatomy of said patient may then be created using the points from the 2-D x-ray images. Using the 2-D x-ray images just taken of said patient by the imaging system in question, a coordinate system can be defined of the imaged portions of the patient. A coordinate point can be defined in the 3-D space of the imaging system reference frame by comparing the relevant positions of the point in each of the 2-D x-ray images. The points of each of the 2-D x-ray images need line up at the same position of the patient's anatomy, for example the user could define an edge of the liver as the position of the point in each of the 2-D x-ray images so when those points are converted into a coordinate point in the 3-D space, the coordinate point aligns with that particular position of the patient's anatomy. This coordinate point may be understood by the imaging system with relation to the imaging system reference frame.

At 1306, the data of the coordinate point in the 3-D coordinate plane within the imaging system reference frame, indicating the location of the coordinate point with respect to the imaging system reference frame, specifically with respect to the table, may then be sent to an AR system. Once obtained by the AR system, the coordinate point may be displayed by the AR device as a virtual overlay within the imaging system reference frame (see FIG. 15).

After 1306, the method 1300 ends.

Figure 14:
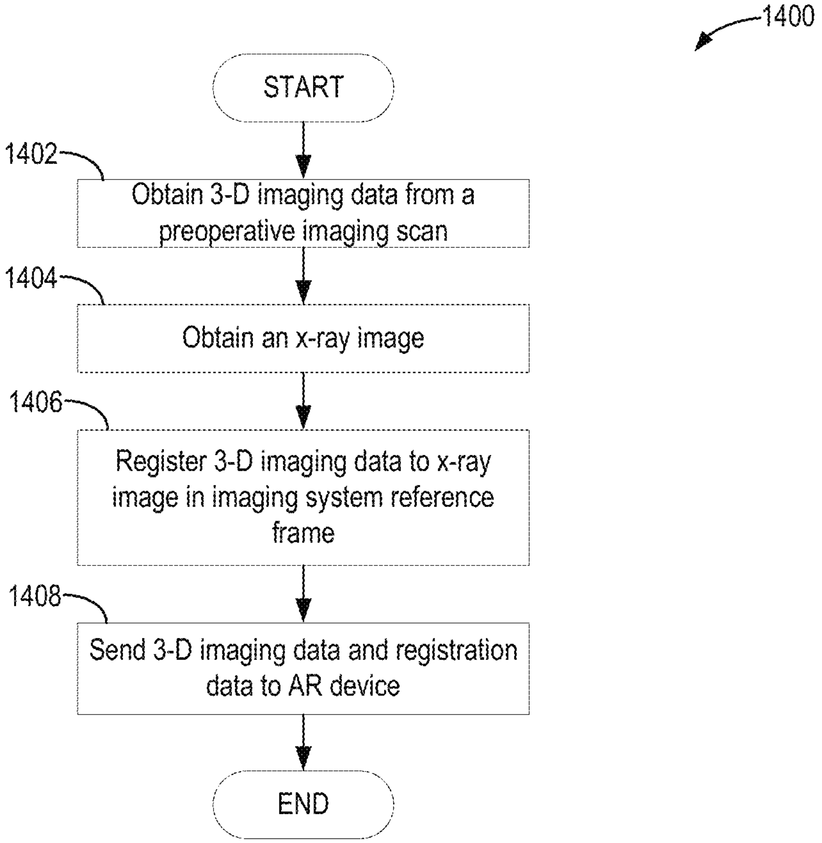
FIG. 14 is a flowchart depicting an example method for patient anatomy localization using a 3-D data set.

FIG. 14 is a flowchart that depicts an exemplary embodiment of a method 1400 for patient anatomy localization using a 3-D data set that may be performed in conjunction with method 1500 to compute data sets to send to the AR device for display. Method 1400 may be executed using computer readable instructions stored in the non-transitory memory of an imaging system (e.g., imaging system 100).

At 1402, a 3-D data set (e.g., a preoperative CT scan or MRI scan) may be obtained from an outside source (e.g., an MRI machine or a helical CT machine). In one embodiment, the 3-D data set may display the target anatomy of the patient that is about to be imaged by an imaging system discussed below.

At 1404, a 2-D x-ray image may be obtained of a patient lying within the imaging system reference frame (the imaging system reference frame may include both a gantry and a table). In one embodiment, this may entail obtaining an intraoperative fluoroscopy x-ray while the patient is lying on an operating table in an operating room.

At 1406, the 3-D data set may be registered to the 2-D x-ray image (e.g., the intraoperative fluoroscopy x-ray). The imaging system may have computer readable instructions stored in its non-transitory memory for extrapolating the anatomy from the 3-D data set to correspond it to the 2-D data set which is known within the imaging system reference frame. A traditional method of corresponding the 3-D data set with the 2-D data set is to provide approximate registration based on a priori information (e.g., estimated location of patient in pre-op imaging reference frame vs location of patient in imaging system reference frame) and then an operator of the imaging system may align common anatomical features between pre-op imaging (e.g., 3-D data set) and x-ray images (2-D data set. This may be done by superimposing (e.g., fusing) a projection image generated from the 3-D data set and the 2-D data set and translating or rotating one of the data sets with relation to the other (e.g., using a user input device such as a keyboard or joystick type user interface). As an example, for abdominal images, alignment may be done via spine features, for example using a front and lateral x-ray view as the 2-D data set. Extrapolating the data of the patient anatomy from the registration of the 3-D data set to the 2-D data may create a coordinate transformation for which to identify the location of the patient's anatomy in his or her current location within the imaging system reference frame.

At 1408, the data from the 3-D data set and the registration data (described above at 1406) may be sent to the AR system. The data of the 3-D data set and the registration data may include the location of the patient anatomy (derived from the 3-D data set and registration data) within the imaging system reference frame, specifically with respect to the table. Once obtained by the AR system, the patient's anatomy may be displayed by the AR device as a virtual overlay within the imaging system reference frame (further explanation provided with reference to FIG. 16).

After 1408, the method 1400 ends.

Figure 15:
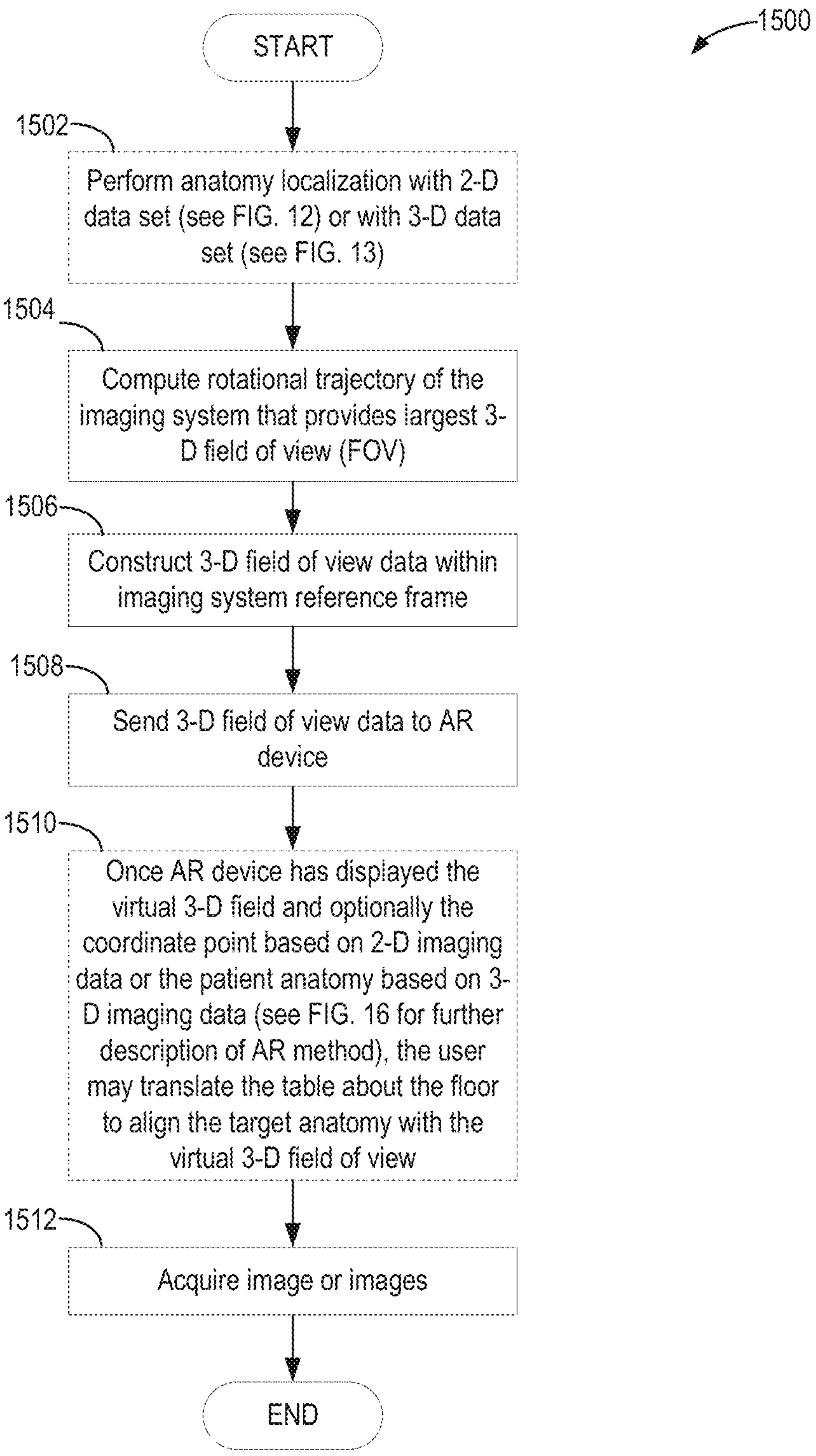
FIG. 15 is a flowchart depicting an example method for CBCT centering with AR optionally using patient anatomy localization with either 2-D data sets or 3-D data set.

FIG. 15 is a high-level flow chart of a method 1500 for aligning a 3-D field of view of the imaging system referenced with respect to FIG. 13 or 14 with the target anatomy of the patient referenced with respect to FIG. 13 or 14. Method 1500 may be optionally performed in conjunction with method 1300 or method 1400. Method 1500 may be executed using computer readable instructions stored in the non-transitory memory of the imaging system (e.g., imaging system 100).

At 1502, patient anatomy localization may be performed as described in method 1300 using 2-D data sets or as described in method 1400 using a 3-D data set and a 2-D x-ray image. In one embodiment, this may result in the AR system receiving data in order to display a coordinate point corresponding to the relevant patient anatomy localized within the imaging system reference frame. This process is further described with respect to FIG. 16.

At 1504, the imaging system may compute the rotational trajectory of the gantry of the imaging system. In one example, the rotational trajectory may be computed so as to provide the largest possible 3-D field of view taking into account image quality constraints and avoiding potential collisions between the gantry and the table or the patient. The imaging system may know the relative geometry of its components, including the distance between a detector and a source of the gantry of the imaging system. The imaging system may compute the position and volume of the largest possible 3-D field of view by defining the distance between the source (e.g., focal point) and the detector, the distance between the source and an isocenter of the imaging system, and the length of an exposed field of view at the detector which at its maximum may be the length of the detector. The diameter of the 3-D field of view, assuming that the gantry is rotated about only one axis so as to define the shape of the 3-D field of view as a cylinder with conical extensions, may be defined as the distance between the source and the isocenter divided by the distance between the source and the detector all multiplied by the length of the exposed field of view at the detector. The calculated diameter of the cylinder may then be used to determine the volume of the 3-D field of view. The diameter of the cylinder can be divided in half to find the radius of the cylinder. The radius may then be squared, multiplied by pi, and multiplied by the predicted width of cone beam at the intersection of each position along the rotation (which defines the height of the cylinder) to find the volume of the cylinder. Finding the total volume of the 3-D field of view that includes conical extensions at bases may also include calculating the volume of one of the cones. Finding the volume of the cone may entail finding the height of the cone and diving it by three. This value may then be multiplied by a radius of the cone base squared (the radius of the cone base may be equal to the radius of the cylinder base) and then multiplied by pi. This value represents the volume of one of the cones, to find the total volume of both cones, the value may be multiplied by two. The volume of the cylinder may be added to the combined volume of the cones to find the total volume of the 3-D field of view. Additionally, the imaging system may compute where an exposed area on the detector will be for each position along the rotational trajectory in order to provide a larger 3-D field of view, as described with reference to FIG. 7.

As stated above, the imaging system knows the positions of its components and therefore knows the values of the relevant distances and lengths in order to compute the 3-D field of view. The imaging system, because it knows the positions of the components (e.g., the detector and signal transmitter), may also know where the 3-D field of view is located within the imaging system reference frame. The 3-D field of view is dependent on the positions of the signal transmitter and the detector. The positions of the detector and the signal transmitter may be altered to bring them closer together or further apart. Changing the positions of the signal transmitter and the detector inherently alters the size of the 3-D field of view. The imaging system may compute a new 3-D field of view for each scan in order to determine the current 3-D field of view in relation to the current positions of and distances between the detector and the signal transmitter.

However, the ideal case described above may be unlikely to occur due to imperfect geometry of the imaging system whereby the axes may not intersect, the cone beam of radiation may not be perfectly centered on the detector, the cone beam of radiation may be asymmetric due to imperfect collimation, and/or the gantry mechanical structure may deform during rotation. These non-idealities may be corrected for by calibrating the geometry of the imaging system 100. This calibration process entails compensating for inaccuracies in the manufacturing process (e.g., via adjustment of alignment of components such as the detector), characterizing system non-idealities, and deriving projection geometry of the imaging system (e.g., by imaging a calibration phantom) as described with reference to FIG. 8. Additionally, location of exposed area on the detector may be computed for each position along the rotational acquisition. This may allow acquisition of a larger 3-D field of view as compared to taking the smallest of all projections.

At 1506, the computed 3-D field of view may be constructed by the imaging system as a data set within the imaging system reference frame. The data set may define the size, shape, and position of the 3-D field of view within the imaging system reference frame. In one embodiment, the imaging system reference frame may contain the relative positions of the gantry, C-arm, and table.

At 1508, the data of the computed 3-D field of view may be sent by the imaging system to the AR device. The data of the computed 3-D field of view may include the location of the imaging system as well as a first location of the computed 3-D field of view with respect to the imaging system reference frame.

At 1510, once the AR device has displayed the virtual 3-D field of view and optionally the coordinate point based on 2-D imaging data or the patient anatomy based on 3-D imaging data (see FIG. 16 description for further description of AR method), the user may translate the table about the floor to align the target anatomy with the virtual 3-D field of view. The translation about the floor may be performed so that the virtual coordinate point or virtual patient anatomy lies within the virtual 3-D field of view as visualized by the AR device. In some embodiments, the coordinate point or patient anatomy may be localized in relation to the imaging system reference frame, which includes the relative position of the table, so that as the table is translated about the floor, the coordinate point or patient anatomy also moves so that the coordinate point remains in the correct location within the patient.

At 1512, once the table (and the patient given that the patient may be lying in direct contact with the table) is positioned as such to align the virtual coordinate point or virtual target anatomy with the virtual 3-D field of view, the imaging system may perform image acquisition as instructed by a user. The imaging system may be responsive to a command to activate the x-ray source to perform such an imaging acquisition.

After 1512, the method 1500 ends.

Figure 16:
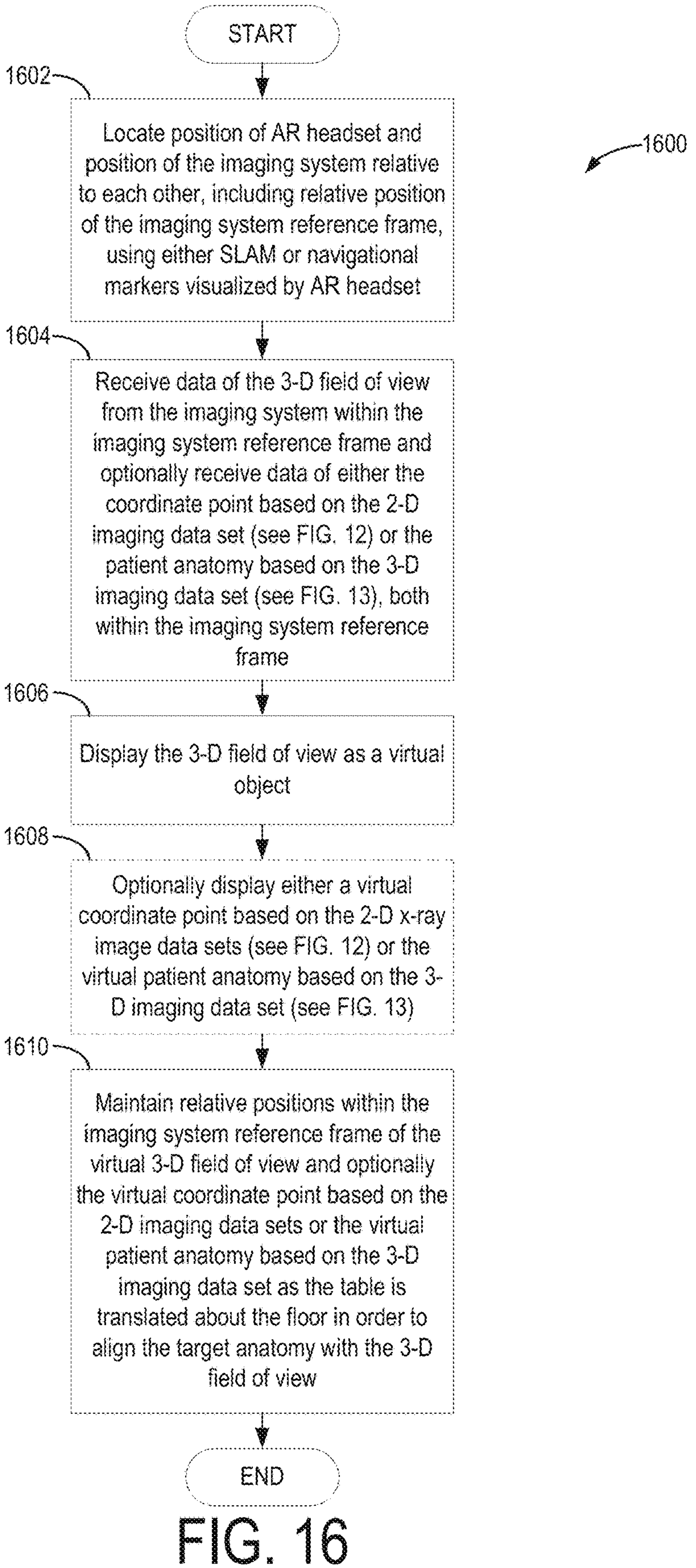
FIG. 16 is a flowchart depicting an example method for AR data acquisition and display of virtual objects.

FIG. 16 is a flow chart of a method 1600 for AR device localization and display of virtual objects. Method 1600 may be performed in conjunction with method 1500 and optionally in conjunction with either method 1300 or method 1400. Method 1600 may be executed using computer readable instructions stored in the non-transitory memory of an augmented reality device (e.g., AR device 900).

At 1602, the AR device may locate its position and its own reference frame with relation to the imaging system position and the imaging system reference frame. The AR device may perform this localization via a plurality of forward facing cameras and sensors using either SLAM (Simultaneous Localization and Mapping) or using navigation markers placed about the room. In some embodiments, the SLAM process may be executed using computer readable instructions stored in the non-transitory memory of the AR device. The forward facing cameras and sensors included in the AR device may image the environment in which the AR device is located and may identify objects and their positions relative to the AR device in order to build a map of the room. Alternatively or additionally, the AR device may visualize and use navigation markers (e.g., QR codes) that have been placed about the room to locate the relative positions of the components in the room, including the imaging system and the imaging system reference frame.

At 1604, the AR device may receive one or more data sets from the imaging system. The data from the imaging system may be usable by the AR device in order to display graphical objects in the AR space. The AR device may receive the data of the 3-D field of view that was computed by the imaging system, as described with respect to FIG. 14. The AR device may also optionally receive the data set of the coordinate point within the imaging system reference frame that was based on data from two or more 2-D x-ray images taken by the imaging system within the imaging system reference frame in addition to the data set of the 3-D field of view (see FIG. 13 description). Alternatively, the AR device may optionally receive a data set of the patient's anatomy within the imaging system reference frame that was based on data from a 3-D imaging data set and the registration data of that 3-D imaging data set to a 2-D x-ray image that was taken by the imaging system within the imaging system reference frame (as was described with reference to FIG. 13) in addition to receiving the data of the 3-D field of view At 1606, the AR device may display a virtual object representative of the 3-D field of view based on the data set of the 3-D field of view at the correct relative location within the imaging system reference frame. The AR device may determine these correct locations based on the data received from the imaging system and the AR device's knowledge of the relative locations of itself and the imaging system, as described above.

At 1608, the AR device may also optionally display a virtual object representative of the coordinate point (in some embodiments, the virtual coordinate point may be displayed in the AR space as a sphere) based on the 2-D imaging data set (as computed with reference to FIG. 13) in the correct location within the imaging system reference frame. Alternatively, the AR device may optionally display a virtual object representative of the relevant patient anatomy based on the 3-D imaging data set and the registration data set (as computed with reference to FIG. 14) in the correct location within the imaging system reference frame. The AR device may determine these correct locations based on the data received from the imaging system and the AR device's knowledge of the relative locations of itself and the imaging system as described above.

At 1610, the AR device may maintain the relative locations of each of the virtual objects it is displaying, as described above, as the table on which the patient is lying is translated about the floor in order to align the 3-D field of view with the target anatomy. In one example, the virtual coordinate point may move within the imaging system reference frame as displayed through the AR headset of the AR device, correlating to the movement of the table because the virtual coordinate point has a fixed position in relation to the table but a movable position with relation to the gantry.

After 1610, the method 1600 ends.

A technical effect of calculating an imaging field of view (FOV) that corresponds to a desired FOV for a rotatable CBCT imaging system and then sending size, shape, and position information of the imaging FOV to an external computing device (e.g., an augmented reality device) for display on the external computing device is that a patient may be more accurately positioned with respect to the imaging system, which may reduce the number of image acquisitions performed on the patient. Additionally, visualizing the desired FOV with relation to a region of interest may save operator time and cost by reducing number of image acquisitions.

The disclosure also provides support for a method, comprising: determining an imaging field of view (FOV) of a rotatable imaging system, including a size and/or shape of the imaging FOV and a position of the imaging FOV relative to the rotatable imaging system, determining a first location of the imaging FOV relative to an environment in which the rotatable imaging system is positioned, and sending information indicating the size and/or shape and the position of the imaging FOV as well as the first location of the imaging FOV relative to the environment to an external computing device. In a first example of the method, the rotatable imaging system comprises a cone-beam computed tomography (CBCT) system including an x-ray source and a detector mounted on a rotatable gantry. In a second example of the method, optionally including the first example, determining the imaging FOV comprises determining the size and/or shape of the imaging FOV based on one or more of a first distance from the x-ray source to an isocenter of the rotatable gantry, a second distance from the x-ray source to the detector, mechanical deformations of the rotatable gantry during rotation, and a predicted exposed area of the detector, and wherein the imaging FOV is positioned at the isocenter. In a third example of the method, optionally including one or both of the first and second examples, the second distance changes during rotation of the rotatable gantry, wherein the x-ray source is configured to emit a cone beam of radiation and wherein the size and/or shape of the imaging FOV is further determined based on a predicted width of the cone beam at the isocenter. In a fourth example of the method, optionally including one or more or each of the first through third examples, determining the first location of the imaging FOV relative to the environment comprises determining a first location of the CBCT system relative to a table having a pedestal with fixed position in the environment, wherein the table further includes a bed configured to change position in the environment. In a fifth example of the method, optionally including one or more or each of the first through fourth examples, the method further comprises: determining a rotational volume of the CBCT system and a second location of the rotational volume relative to the environment, the rotational volume defined by a rotational trajectory of the x-ray source around one or more rotational axes, and sending information indicating the rotational volume and the second location to the external computing device. In a sixth example of the method, optionally including one or more or each of the first through fifth examples, sending the information to the external computing device comprises sending the information to an augmented reality device, wherein the information is usable by the augmented reality device to generate a graphical representation of the imaging FOV for display via the augmented reality device. In a seventh example of the method, optionally including one or more or each of the first through sixth examples, the method further comprises: determining a second location of a target region of interest (ROI) of a patient to be imaged by the rotatable imaging system, the second location of the target ROI determined relative to the environment, and sending information indicating the second location to the external computing device. In an eighth example of the method, optionally including one or more or each of the first through seventh examples, determining the second location of the target ROI comprises determining the second location of the target ROI based on one or more images of the patient acquired with the rotatable imaging system.

The disclosure also provides support for a cone-beam computed tomography (CBCT) imaging system, comprising: an x-ray source and a detector mounted on a rotatable gantry, a processor, and memory storing instructions executable by the processor to: determine an imaging field of view (FOV) of CBCT system, including a size and/or shape of the imaging FOV and a position of the imaging FOV relative to the rotatable gantry, determine a first location of the imaging FOV relative to an environment in which the CBCT system is positioned, send information indicating the size and/or shape and the position of the imaging FOV as well as the first location of the imaging FOV relative to the environment to an external computing device, and responsive to a command to initiate image acquisition, activate the x-ray source and detector and rotate the rotatable gantry around a patient. In a first example of the system, determining the imaging FOV comprises determining the size and/or shape of the imaging FOV based on one or more of a first distance from the x-ray source to an isocenter of the rotatable gantry, a second distance from the x-ray source to the detector, mechanical deformations of the rotatable gantry during rotation, and a predicted exposed area of the detector, and wherein the imaging FOV is positioned at the isocenter. In a second example of the system, optionally including the first example, the second distance changes during rotation of the rotatable gantry, wherein the x-ray source is configured to emit a cone beam of radiation, and wherein the size and/or shape of the imaging FOV is further determined based on a predicted width of the cone beam at the isocenter. In a third example of the system, optionally including one or both of the first and second examples, determining the first location of the imaging FOV relative to the environment comprises determining a location of the CBCT imaging system relative to a table having a pedestal with a fixed position in the environment, wherein the table further includes a bed configured to change position in the environment. In a fourth example of the system, optionally including one or more or each of the first through third examples, sending the information to the external computing device comprises sending the information to an augmented reality device, wherein the information is usable by the augmented reality device to generate a graphical representation of the imaging FOV for display via the augmented reality device.

The disclosure also provides support for a method, comprising: determining, via a processor executing instructions stored in memory of an imaging system, an imaging field of view (FOV) of the imaging system, the imaging system including an x-ray source and a detector mounted on a rotatable gantry and the imaging FOV including a size and/or shape of the imaging FOV and a position of the imaging FOV relative to the rotatable gantry, determining, via the processor executing the instructions stored in memory of the imaging system, a first location of the rotatable gantry relative to an environment in which the imaging system is positioned, sending, from the imaging system, information indicating the size and the position of the imaging FOV as well as the first location to an augmented reality device, and displaying, on a see-through display of the augmented reality device, a graphical object, the graphical object sized and positioned on the see-through display based on the information received from the imaging system and a second location of the augmented reality device within the environment. In a first example of the method, the method further comprises: determining, via the processor executing the instructions stored in memory of the imaging system, a third location of a target region of interest (ROI) of a patient to be imaged by the imaging system, the third location of the target ROI determined relative to the environment, and sending information indicating the third location to the augmented reality device. In a second example of the method, optionally including the first example, determining the third location of the target ROI comprises determining the third location of the target ROI based on one or more images of the patient acquired with the imaging system. In a third example of the method, optionally including one or both of the first and second examples, the method further comprises: displaying, on the see-through display of the augmented reality device, a second graphical object positioned on the see-through display based on the third location of the target ROI and the second location of the augmented reality device. In a fourth example of the method, optionally including one or more or each of the first through third examples, determining the imaging FOV comprises determining the size and/or shape of the imaging FOV based on a first distance from the x-ray source to an isocenter of the rotatable gantry, a second distance from the x-ray source to the detector, mechanical deformations of the rotatable gantry during rotation, and a predicted exposed area of the detector, and wherein the imaging FOV is positioned at the isocenter. In a fifth example of the method, optionally including one or more or each of the first through fourth examples, the method further comprises: responsive to a command to initiate image acquisition, activating, via the processor executing the instructions stored in memory of the imaging system, the x-ray source and detector and rotating the rotatable gantry around a patient.

In another representation, a method for a cone-beam computed tomography (CBCT) system including an x-ray source and a detector mounted on a rotatable gantry comprises controlling the x-ray source, the detector, and the rotatable gantry to acquire one or more images of a patient; determining an imaging field of view (FOV) of the CBCT system, including a size of the imaging FOV and a position of the imaging FOV relative to the rotatable gantry; determining a first location of the imaging FOV relative to an environment in which the CBCT system is positioned; determining a second location of a target region of interest (ROI) of the patient based on the one or more images of the patient; and sending information indicating the size and the position of the imaging FOV, the first location of the imaging FOV, and the second location of the target ROI to an external computing device.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

determining an imaging field of view (FOV) of a rotatable imaging system, including a size and/or a shape of the imaging FOV of the rotatable imaging system and a position of the imaging FOV relative to the rotatable imaging system;

determining a first location of the imaging FOV of the rotatable imaging system relative to an environment in which the rotatable imaging system is positioned; and sending information indicating the size and/or the shape and the position of the imaging FOV of the rotatable imaging system as well as the first location of the imaging FOV of the rotatable imaging system relative to the environment to an external computing device.

2. The method of claim 1, wherein the rotatable imaging system comprises a cone-beam computed tomography (CBCT) system including an x-ray source and a detector mounted on a rotatable gantry.

3. The method of claim 2, wherein determining the imaging FOV of the rotatable imaging system comprises determining the size and/or the shape of the imaging FOV of the rotatable imaging system based on one or more of a first distance from the x-ray source to an isocenter of the rotatable gantry, a second distance from the x-ray source to the detector, mechanical deformations of the rotatable gantry during rotation, and a predicted exposed area of the detector, and wherein the imaging FOV of the rotatable imaging system is positioned at the isocenter of the rotatable gantry.

4. The method of claim 3, wherein the second distance from the x-ray source to the detector changes during rotation of the rotatable gantry, wherein the x-ray source is configured to emit a cone beam of radiation, and wherein the size and/or the shape of the imaging FOV of the rotatable imaging system is further determined based on a predicted width of the cone beam of radiation at the isocenter of the rotatable gantry.

5. The method of claim 2, wherein determining the first location of the imaging FOV of the rotatable imaging system relative to the environment comprises determining a first location of the CBCT system relative to a table having a pedestal with a fixed position in the environment, wherein the table further includes a bed configured to change position in the environment.

6. The method of claim 2, further comprising determining a rotational volume of the CBCT system and a second location of the rotational volume relative to the environment, the rotational volume of the CBCT system defined by a rotational trajectory of the x-ray source around one or more rotational axes, and sending information indicating the rotational volume of the CBCT system and the second location of the rotational volume to the external computing device.

7. The method of claim 1, wherein sending the information to the external computing device comprises sending the information to an augmented reality device, wherein the information is usable by the augmented reality device to generate a graphical representation of the imaging FOV of the rotatable imaging system for display via the augmented reality device.

8. The method of claim 1, further comprising determining a second location of a target region of interest (ROI) of a patient to be imaged by the rotatable imaging system, the second location of the target ROI of the patient determined relative to the environment, and sending information indicating the second location of the target ROI of the patient to the external computing device.

9. The method of claim 8, wherein determining the second location of the target ROI of the patient comprises determining the second location of the target ROI of the patient based on one or more images of the patient acquired with the rotatable imaging system.

10. A cone-beam computed tomography (CBCT) imaging system, comprising:

a rotatable gantry;

an x-ray source and a detector mounted on the rotatable gantry;

a processor; and a memory storing instructions executable by the processor to:

determine an imaging field of view (FOV) of the CBCT imaging system, including a size and/or a shape of the imaging FOV of the CBCT imaging system and a position of the imaging FOV of the CBCT imaging system relative to the rotatable gantry;

determine a first location of the imaging FOV of the CBCT imaging system relative to an environment in which the CBCT imaging system is positioned;

send information indicating the size and/or the shape and the position of the imaging FOV of the CBCT imaging system as well as the first location of the imaging FOV of the CBCT imaging system relative to the environment to an external computing device; and responsive to a command to initiate image acquisition, activate the x-ray source and the detector, and rotate the rotatable gantry around a patient.

11. The CBCT imaging system of claim 10, wherein determining the imaging FOV of the CBCT imaging system comprises determining the size and/or the shape of the imaging FOV of the CBCT imaging system based on one or more of a first distance from the x-ray source to an isocenter of the rotatable gantry, a second distance from the x-ray source to the detector, mechanical deformations of the rotatable gantry during rotation, and a predicted exposed area of the detector, and wherein the imaging FOV of the CBCT imaging system is positioned at the isocenter of the rotatable gantry.

12. The CBCT imaging system of claim 11, wherein the second distance from the x-ray source to the detector changes during rotation of the rotatable gantry, wherein the x-ray source is configured to emit a cone beam of radiation, and wherein the size and/or the shape of the imaging FOV of the CBCT imaging system is further determined based on a predicted width of the cone beam of radiation at the isocenter of the rotatable gantry.

13. The CBCT imaging system of claim 10, wherein determining the first location of the imaging FOV of the CBCT imaging system relative to the environment comprises determining a location of the CBCT imaging system relative to a table having a pedestal with a fixed position in the environment, wherein the table further includes a bed configured to change position in the environment.

14. The CBCT imaging system of claim 10, wherein sending the information to the external computing device comprises sending the information to an augmented reality device, wherein the information is usable by the augmented reality device to generate a graphical representation of the imaging FOV of the CBCT imaging system for display via the augmented reality device.

15. A method, comprising:

determining, via a processor executing instructions stored in a memory of an imaging system, an imaging field of view (FOV) of the imaging system, the imaging system including an x-ray source and a detector mounted on a rotatable gantry, and the imaging FOV of the imaging system including a size and/or a shape of the imaging FOV and a position of the imaging FOV relative to the rotatable gantry;

determining, via the processor executing the instructions stored in the memory of the imaging system, a first location of the rotatable gantry relative to an environment in which the imaging system is positioned;

sending, from the imaging system, information indicating the size and the position of the imaging FOV of the imaging system as well as the first location to an augmented reality device; and displaying, on a see-through display of the augmented reality device, a graphical object, the graphical object sized and positioned on the see-through display based on the information received from the imaging system and a second location of the augmented reality device within the environment.

16. The method of claim 15, further comprising determining, via the processor executing the instructions stored in the memory of the imaging system, a third location of a target region of interest (ROI) of a patient to be imaged by the imaging system, the third location of the target ROI of the patient determined relative to the environment, and sending information indicating the third location to the augmented reality device.

17. The method of claim 16, wherein determining the third location of the target ROI of the patient comprises determining the third location of the target ROI of the patient based on one or more images of the patient acquired with the imaging system.

18. The method of claim 16, further comprising displaying, on the see-through display of the augmented reality device, a second graphical object positioned on the see-through display of the augmented reality device based on the third location of the target ROI of the patient and the second location of the augmented reality device within the environment.

19. The method of claim 15, wherein determining the imaging FOV of the imaging system comprises determining the size and/or the shape of the imaging FOV based on a first distance from the x-ray source to an isocenter of the rotatable gantry, a second distance from the x-ray source to the detector, mechanical deformations of the rotatable gantry during rotation, and a predicted exposed area of the detector, and wherein the imaging FOV of the imaging system is positioned at the isocenter of the rotatable gantry.

20. The method of claim 15, further comprising, responsive to a command to initiate image acquisition, activating, via the processor executing the instructions stored in the memory of the imaging system, the x-ray source and the detector, and rotating the rotatable gantry around a patient.

* * * * *